(12) United States Patent
Pak et al.

(10) Patent No.: US 11,564,701 B2
(45) Date of Patent: Jan. 31, 2023

(54) APPARATUS FOR AUTOMATED OPENING OF CRANIOTOMIES FOR MAMMALIAN BRAIN ACCESS

(71) Applicant: Massachusetts Institute of Technology, Cambridge, MA (US)

(72) Inventors: Nikita Pak, Allston, MA (US); Justin P. Kinney, Quincy, MA (US); Edward S. Boyden, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 176 days.

(21) Appl. No.: 17/088,494

(22) Filed: Nov. 3, 2020

(65) Prior Publication Data
US 2021/0298769 A1 Sep. 30, 2021

Related U.S. Application Data

(62) Division of application No. 15/096,256, filed on Apr. 11, 2016, now Pat. No. 10,820,914.

(60) Provisional application No. 62/146,201, filed on Apr. 10, 2015.

(51) Int. Cl.
| | | |
|---|---|---|
| A61B 17/00 | (2006.01) | |
| A61B 17/16 | (2006.01) | |
| A61B 34/30 | (2016.01) | |
| A61B 34/32 | (2016.01) | |
| A61B 90/10 | (2016.01) | |

(52) U.S. Cl.
CPC ......... *A61B 17/1695* (2013.01); *A61B 34/30* (2016.02); *A61B 34/32* (2016.02); *A61B 90/10* (2016.02); *A61B 2017/00026* (2013.01)

(58) Field of Classification Search
CPC combination set(s) only.
See application file for complete search history.

(56) References Cited

U.S. PATENT DOCUMENTS

2014/0276839 A1* 9/2014 Forman ............... A61B 10/025
173/2

* cited by examiner

*Primary Examiner* — Sameh R Boles
(74) *Attorney, Agent, or Firm* — Norma E. Henderson

(57) ABSTRACT

An automated craniotomy opening apparatus includes a drilling apparatus with a drilling tip, at least one drilling apparatus positioning device, a detection device, and a computer processor that automatically controls the drilling apparatus, the positioning device, and the detection device. A method for automated opening of craniotomies includes, under automatic control of a computer processor, drilling into a skull for a predetermined distance and determining when there is a conductance drop near the drilling tip that indicates skull breakthrough. If the conductance is not below a predetermined threshold, drilling continues iteratively manner until conductance is below the threshold. A craniotomy pattern may be predetermined and automatically drilled under control of the processor. A cranial window may be created by drilling along a path that interpolates between holes to form the circumference of the window. Determining conductance may include use of an impedance detection circuit.

14 Claims, 18 Drawing Sheets

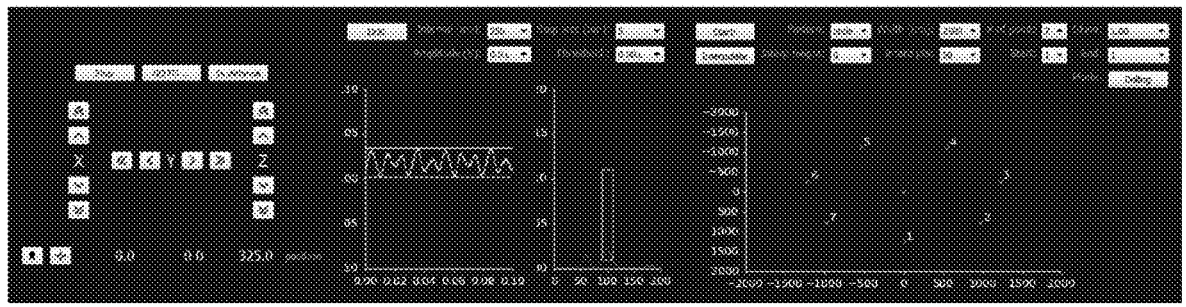
Fig. 24
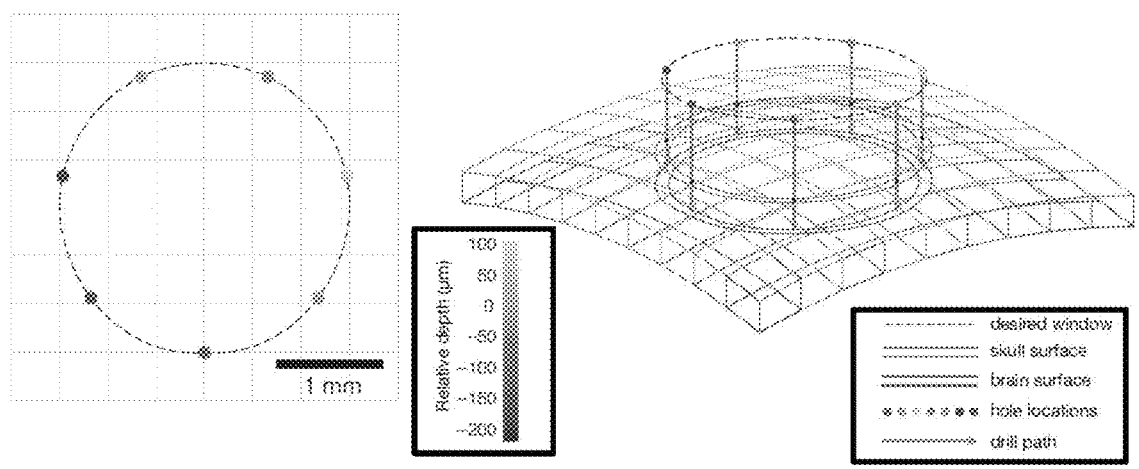
Fig. 25A                    Fig. 25B

Fig. 26A    Fig. 26B
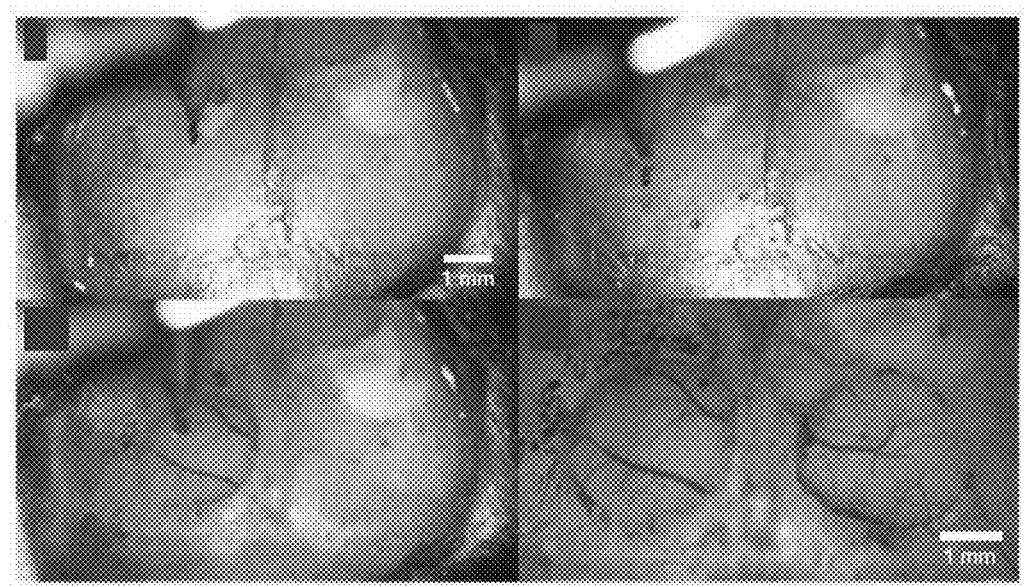
Fig. 26C    Fig. 26D
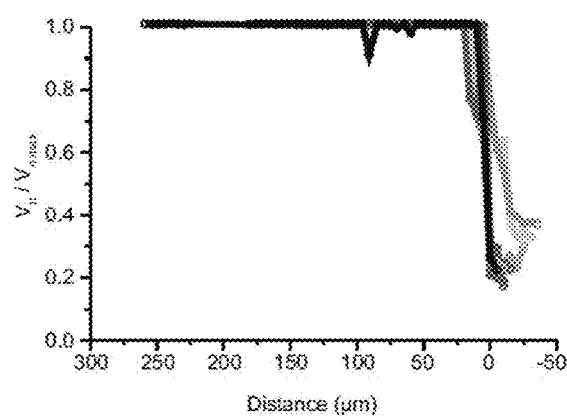 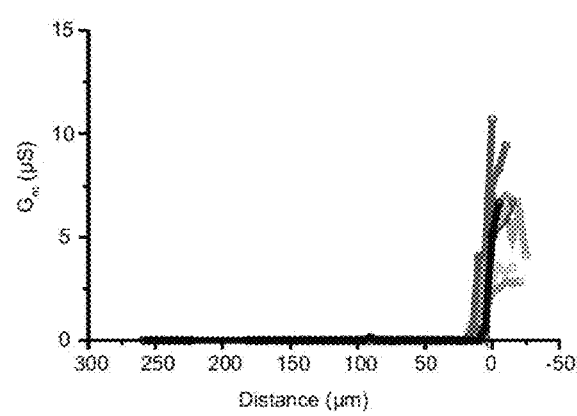
Fig. 27A    Fig. 27B

APPARATUS FOR AUTOMATED OPENING OF CRANIOTOMIES FOR MAMMALIAN BRAIN ACCESS

RELATED APPLICATIONS

This application is a divisional of U.S. patent application Ser. No. 15/096,256, filed Apr. 11, 2016, now U.S. Pat. No. 10,820,914, issued Nov. 3, 2020, which claims the benefit of U.S. Provisional Application Ser. No. 62/146,201, filed Apr. 10, 2015, the entire disclosures of which are herein incorporated by reference.

STATEMENT REGARDING FEDERALLY SPONSORED RESEARCH OR DEVELOPMENT

This invention was made with Government support under Grant Nos. NS087724, R01 EY023173, R01 MH103910, and R43 MH101943, awarded by the National Institutes of Health, and under Grant Nos. CBET1053233 and DMS1042134, awarded by the National Science Foundation. The Government has certain rights in the invention.

INCORPORATION BY REFERENCE OF MATERIAL SUBMITTED IN COMPUTER-READABLE FORMAT

This application contains a computer program listing appendix submitted in computer-readable format as an electronically-filed text file under the provisions of 37 CFR 1.96 and herein incorporated by reference. The computer program listing appendix text file includes, in ASCII format, the following files: gui.py, neurostar.py, nidaq.py, and robot_retinotopy._GUI.py.

FIELD OF THE TECHNOLOGY

The present invention relates to medical procedures and, in particular, to automated craniotomies.

BACKGROUND

Many neuroscience techniques, such as optogenetics and in vivo electrophysiology, require access to the brain. Ideally, craniotomies could be performed in a repeatable and automated fashion, without damaging the underlying brain tissue.

Automation of craniotomies could in principle enable in vivo neuroscience experiments to be performed with greater ease, reproducibility, and throughput than it is possible for human surgical operators to achieve. These benefits could in turn result in better repeatability of experiments and higher quality neural data, as well as the ability to deploy neural recording or stimulation probes in complex 3-D geometries that target multiple brain regions [Zorzos, A. N., Scholvin, J., Boyden, E. S., & Fonstad, C. G. Three-dimensional multiwaveguide probe array for light delivery to distributed brain circuits. Opt Lett. 37(23): 4841-4843, 2012]. In vivo whole cell patch clamp neural recording [Kodandaramaiah S. B., Franzesi G. T., Chow B. Y., Boyden E. S., Forest C. R. Automated whole-cell patch-clamp electrophysiology of neurons in vivo. Nat Methods. 9(6): 585-587, 2012] has previously been automated, discovering that a glass micropipette being lowered into the living mouse brain undergoes a stereotyped small increase in pipette resistance upon encountering a cell, enabling building a robot that can automatically patch clamp neurons in the living mammalian brain.

Automated craniotomies have been attempted before. Some current methods for performing automated craniotomies use force feedback [Loschak, P., Xiao, K., Pei, H., Kesner, S. B., Thomas, A. J., and Walsh, C. Cranial drilling tool with retracting drill bit upon skull penetration, Proceedings of the Design of Medical Devices Conference, Apr. 10-12, 2012, Minneapolis, Minn.: University of Minnesota Medical Devices Center, 2012; Pohl, B. M., Schumacher, A., & Hofmann, U. G. (2011). Towards an automated, minimal invasive, precision craniotomy on small animals. 2011 5th International IEEE/EMBS Conference on Neural Engineering, 302-305], imaging to map out the skull geometry and then open loop operation [Cunha-Cruz, V., Follmann, a, Popovic, a, Bast, P., Wu, T., Heger, S., Radermacher, K. (2010). Robot- and computer-assisted craniotomy (CRANIO): from active systems to synergistic man/machine interaction. Proceedings of the Institution of Mechanical Engineers, Part H: Journal of Engineering in Medicine, 224(3), 441-452], and femtosecond lasers to ablate the skull [Jeong, D. C., Tsai, P. S., & Kleinfeld, D. (2013). All-optical osteotomy to create windows for transcranial imaging in mice. Optics Express, 21(20), 23160-8]. However, it is unclear whether these methods can achieve better than millimetric resolution. Open-loop systems require CT scanning of the skull to measure the skull thickness, which is both expensive and involves dangerous x-rays. Use of femtosecond lasers is also an expensive proposition.

SUMMARY

When drilling through a skull, a stereotypical increase in conductance can be observed when the drill bit passes through the skull base, with a sudden increase in the electrical conductance between the drill and body indicating when the drill is in the skull but not touching the brain. Lowering a drill through the skull until an increase in the conductance between the drill and the body indicates that the drill is in the skull is of use in automating craniotomy surgeries. The present invention employs a methodology that leverages this discovery.

A robot was implemented to perform automated craniotomies using conductance measurements, and the precision of the drilling was characterized. Using the invention, craniotomies can be done reliably, and without any bleeding from the meninges or brain, even in precisely aligned arrays. A commercially available motorized stereotaxic apparatus was modified and outfitted with a measurement circuit based on the same principle. Using the same detection method, it is possible to create larger windows in the skull by drilling multiple small craniotomies in a ring, interpolating in between them via milling, and removing the skull piece thus isolated. Robots utilizing this approach may find widespread use for in vivo neuroscience experiments that require either large cranial windows or multisite injector, electrode, fiber, or other device insertion through arrays of craniotomies.

In one aspect, the invention is an architecture for a robotic device that can perform this methodology, along with two implementations—one based on custom hardware, one based on commercially available hardware—that can automatically detect such changes, and create large numbers of precise craniotomies, even in a single skull. This technique can be adapted to automatically drill cranial windows several millimeters in diameter. Such robots are not only useful for helping neuroscientists perform routine craniotomies more reliably, but can also be used to create precisely aligned arrays of craniotomies that would be difficult or impossible to drill by hand.

In one aspect of the invention, a method for automated opening of craniotomies includes the steps of positioning a craniotomy apparatus drilling tip at a starting position relative to a target skull and performing a series of steps under the control of a computer processor configured with control software for operating the craniotomy apparatus. The steps include drilling into the target skull with the drilling tip for a predetermined distance; after drilling, determining the conductance near the drilling tip; if the conductance is below a predetermined threshold, returning the drilling tip to a home position; and if the conductance is not below the predetermined threshold, repeating the steps of drilling and determining until the conductance exceeds the predetermined threshold. The step of determining the conductance may include, under the control of the computer processor, measuring impedance with an impedance detection circuit and calculating the conductance using the measured impedance. The step of measuring impedance may include sending a signal through the impedance circuit to the drilling tip; detecting a voltage at the target skull; and sending a signal representing the detected voltage from the impedance circuit to the computer processor, or may include sending a signal at a predetermined voltage through the impedance circuit to the target skull; detecting a voltage at the drilling tip; and sending a signal representing the detected voltage from the impedance circuit to the computer processor. The step of calculating may include determining a voltage drop across the impedance circuit.

The method may include predetermining a drill hole pattern comprising a plurality of craniotomies to be drilled in the target skull and creating the drill hole pattern by drilling the plurality of craniotomies. The predetermined drill hole pattern may be selected to facilitate creation of a cranial window in the target skull. The cranial window may be created by drilling along a path that interpolates between the holes to form the circumference of the cranial window.

In another aspect of the invention, an automated craniotomy opening apparatus includes a craniotomy drilling apparatus with a drilling tip, at least one craniotomy drilling apparatus positioning device connected to the craniotomy drilling apparatus, a detection device connected to the drilling tip or drill base, and a computer processor specially configured and connected to control the craniotomy drilling apparatus, the craniotomy drilling apparatus positioning device, and the detection device. The computer processor is programmed to perform the steps of positioning the drilling tip with respect to the target skull at a predetermined position for drilling; drilling into the target skull with the drilling tip for a predetermined distance; after drilling, determining the conductance near the drilling tip using the detection device; if the conductance is below a predetermined threshold, returning the drilling tip to a home position; and if the conductance is not below the predetermined threshold, repeating the steps of drilling and determining until the conductance exceeds the predetermined threshold. The detection device may include an impedance detection circuit, which may include a signal source, a sense resistor in series with the signal source, and an output for sending the detected impedance to the computer processor. The detection device may be attached to the drilling tip in a manner that permits measurements to be made while the drilling apparatus is running. The drilling tip may be a blunt-tipped end mill. The positioning apparatus may be a motorized stereotaxic stage connected to the drilling apparatus.

BRIEF DESCRIPTION OF THE DRAWINGS

Other aspects, advantages and novel features of the invention will become more apparent from the following detailed description of the invention when considered in conjunction with the accompanying drawings, wherein:

FIGS. 2-6A-B depict aspects of the design and implementation of an example autodrilling robot for performing the method of FIG. 1, according to one aspect of the invention, wherein:

FIG. 2 is a diagram of an example electrical impedance measurement circuit suitable for use in the invention, FIG. 4 depicts an example custom-built autodrilling robot according to one aspect of the invention, FIG. 5 depicts example drill bits usable in the implementation of FIG. 4, FIG. 6A is a graph of normalized electric potential across the drill and mouse, as a function of frequency, as a dental burr in an example experimental setup is lowered into the skull for seven different mice.

FIGS. 7-10A-B depict implementation aspects of the method for autodrilling, and validation thereof, when run on the robot of FIGS. 2-5, according to further aspects of the invention, wherein:

FIG. 7 is a representative CT scan of a skull, exhibiting an experimental drilling pattern used to produce the data of FIGS. 8A-B, FIG. 9 is a representative CT scan of another skull, exhibiting an experimental drilling pattern used to produce the data of FIGS. 10A-B, FIG. 10A is a plot of craniotomy hole size as a function of final stopping normalized electric potential using the drilling pattern of FIG. 9 and the custom-made automated craniotomy robot.

FIGS. 11-20 relate to a specific example implementation of a custom-built system according to one aspect of the invention, wherein:

FIG. 11 depicts minigrabbers that are used to connect to the drill and to the body of the animal in the example implementation of a device according to the invention, FIG. 12 depicts the front panel of the control display used in the example implementation, FIG. 13 is a schematic flowchart depicting the steps by which the example system initializes the motors and then waits for the user to position the drill in the correct location, FIG. 15 depicts the pattern in which the drill is moved in a preferred embodiment, FIG. 16 is a schematic flowchart depicting the steps by which the example system implements an optional procedure intended to save drilling time, FIGS. 19 and 20 are schematic flowcharts depicting the steps by which the example system retracts the drill and completes the program.

FIGS. 21-24 relate to a specific example modified commercial system implementation according to one aspect of the invention, wherein:

FIG. 21 is a schematic of an example implementation of a system for performing automated craniotomies utilizing a modification of the NeuroStar motorized stereotaxic, according to one aspect of the invention, FIG. 23 is an example implementation of a measurement circuit useable in the modified commercial system implementation, and FIG. 24 is a screenshot of an example embodiment of a graphical user interface useable with the modified commercial system implementation.

FIGS. 25A-B and 26A-D depict an exemplary procedure for drilling large cranial windows according to other aspects of the invention, wherein:

FIGS. 25A and 25B depict windows that were created after drilling a series of test holes, and FIG. 26A-D depict the steps involved in creating two cranial windows in an actual mouse skull.

FIGS. 27A-B and 28A-B depict example results from autodrilling experiments according to aspects of the invention, wherein:

FIG. 27A is a graph of normalized electric potential vs. distance traveled, for 10 holes in one mouse skull, FIG. 27B is a graph of electrical conductance vs. distance traveled for all 10 craniotomies of FIG. 27A, FIG. 28A is a plot of hole size, measured at the base of the skull, measured using x-ray micro-computed tomography (CT), as a function of final normalized electric potential, with the drill stopping when various normalized electrical potentials were reached, and FIG. 28B is a plot of craniotomy hole size vs. electrical conductance for the data of FIG. 28A.

DETAILED DESCRIPTION

The invention is method for performing precise craniotomies, based on conductance measurements taken while lowering a drill bit through the skull, along with devices for performing the method. When drilling through the skull, a stereotypical increase in conductance can be observed when the drill bit passes through the skull base. A circuit is used to measure this change in order to precisely determine when to stop drilling. This method has been applied to robotic drilling devices that can automatically stop at the precise moment when the skull has been drilled through. This prevents damage to the brain and allows researchers to create small, closely spaced craniotomies with little training. Also, this method has been used to create complex three-dimensional craniotomies by recording the depth location of several small craniotomies in order to create a profile of the inner surface of the skull. The method can further be advantageously adapted to automatically drill cranial windows several millimeters in diameter.

In one aspect, the invention is an architecture for a robotic device that can perform the method of the invention. Two specific embodiments of the device have been implemented—one based on custom hardware and one based on commercially available hardware. The device can automatically detect conductance changes and create large numbers of precise craniotomies, even in a single skull. Such robots are not only useful for helping neuroscientists perform routine craniotomies more reliably, but can also be used to create precisely aligned arrays of craniotomies that would be difficult or impossible to drill by hand.

The automated craniotomy robot uses a signal to automatically detect when the drill bit has gone through the skull so that it can stop drilling and not damage the brain. A small AC voltage (1 mV) is sent through the drill bit and the body of the mouse and the amplitude of this signal is measured by a computer program. Bone is a very good electrical resistor, so that when the drill bit pierces through the skull, a noticeable increase in conductance signifies when to stop the robot from drilling further down.

Figure 1:
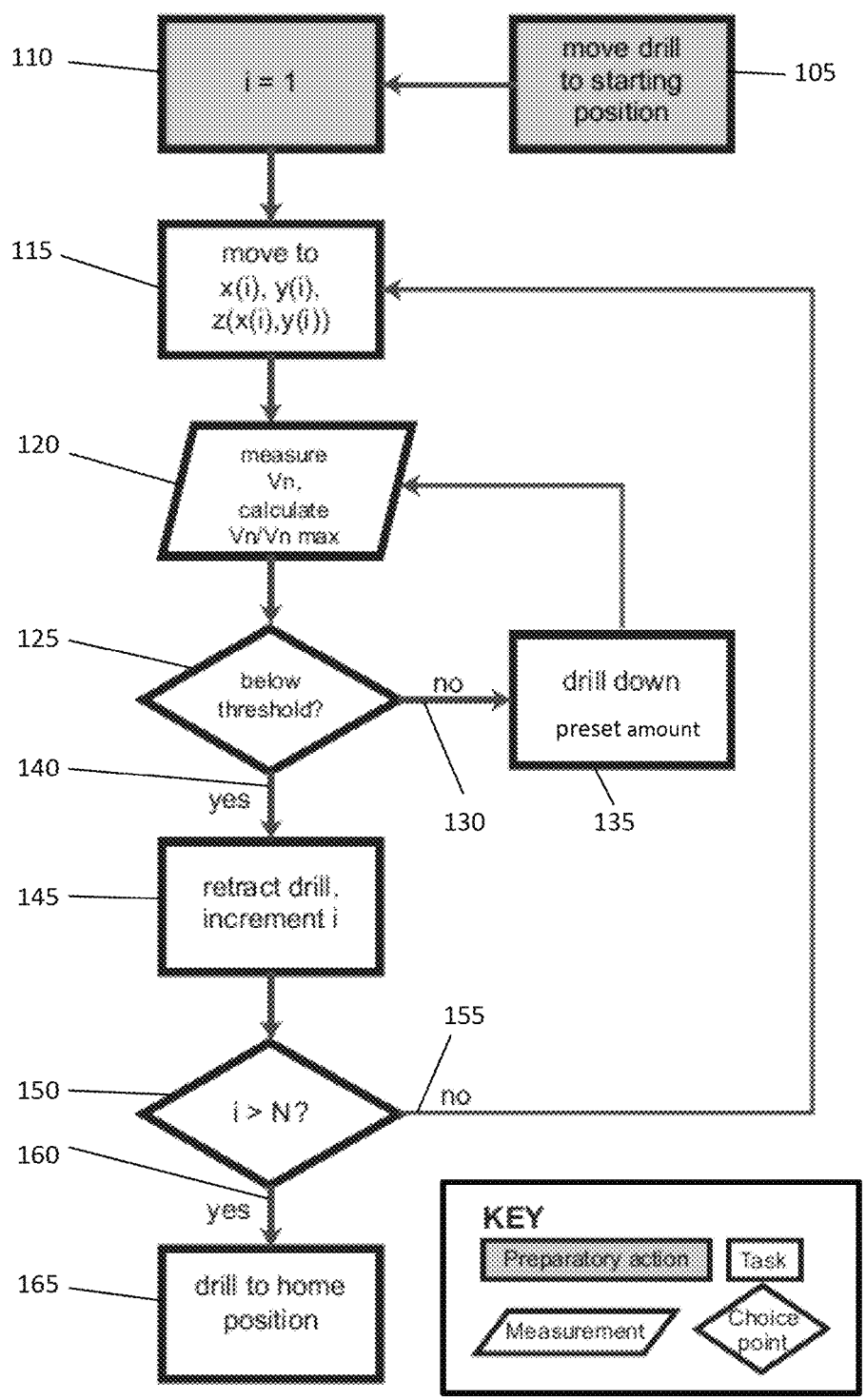
FIG. 1 is a flowchart of an embodiment of a method for craniotomy autodrilling, according to one aspect of the invention.

FIG. 1 is a flowchart of an embodiment of the method for autodrilling, according to one aspect of the invention. As shown in FIG. 1, the drill is moved 105 to the starting position, i is set 110 to 1, and the drill is moved 115 to location x(i), y(i), z(x(i), y(i)). $V_n$ is measured and $V_n/V_n$ max calculated 120 and compared 125 to the threshold. If the result is not below 130 the threshold, the apparatus drills down 135 a prespecified amount and then returns to measurement and calculation step 120. If the result is below 140 the threshold, the drill is retracted 145 and i is incremented and compared 150 to a maximum i (N). If not greater 155 than the maximum, the drill is moved 115 relative to the new value of i. If i is greater 160 than the maximum, the drill is returned 165 to the home position.

An impedance detection circuit, threshold value, and techniques for minimizing the current used are all aspects of physical implementations of the invention. Preferred embodiments of the impedance detection circuit utilize components that can be found in most laboratories and can be added on to an existing surgery setup with only a few modifications.

The threshold value may be determined through trials and should be chosen to be a balance between being high enough to ensure that the drill does not go too far and damage the brain, but low enough to consistently create craniotomies without residual bone being left behind that could damage probes or impede visual observations of the brain.

Figure 2:
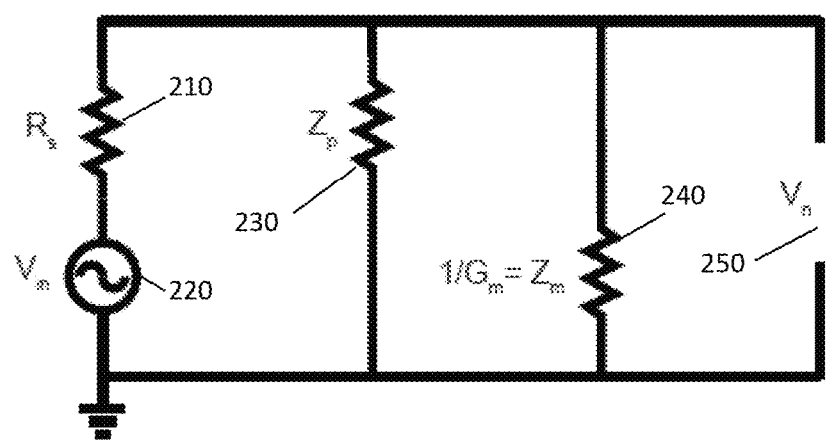

FIG. 2 is a diagram of an example electrical impedance measurement circuit suitable for use in the invention. The basic impedance circuit consists of a sense resistor, an AC signal source, and a computer program to capture and detect the signal. Shown in FIG. 2 are sense resistor 210, function generator (or DAQ) 220, parasitics 230, mouse resistance 240, and DAQ analog input 250. It will be clear to one of skill in the art that, while specific components are set forth in this example, other components providing the same functionality would be suitable and could be advantageously employed in the construction of an impedance circuit usable in the invention.

Several techniques have been implemented in order to minimize the current necessary for the impedance detection circuit to work. Given the 200 μm diameter drill bits typically used, the current density levels are nearly two orders of magnitude below the lowest current density values published capable of stimulating brain tissue. The sense resistor was specifically chosen to be large enough to minimize the amount of current applied (so as to ensure no damage to the brain or stimulation of neurons), but still allows the detection of the signal. A Fourier transform is used to detect the signal that might otherwise be too small to measure.

In an example implementation, the circuit works by sending a sine wave from either a function generator (such as, but not limited to, part 33250A, Agilent, Santa Clara, Calif.) or from a LabVIEW (LabVIEW 2011, National Instruments, Austin, Tex.) data acquisition board (DAQ) (NI USB-6353, National Instruments, Austin, Tex.), or other similar device, through a sense resistor (681 kW for FIGS. 6A-B) and a wire in contact with either the drill body or directly in contact with the drill bit. The cable conducts the electrical signal from the function generator or DAQ to the drill and from the mouse back to the oscilloscope or the DAQ. This cable consists of a coaxial cable, a pair of twisted wires, or a shielded USB cable. The wire mesh shields of the coaxial and USB cables were connected to earth ground to minimize the effects of environmental noise. The rear paw of the mouse made electrical contact to the ground lead of this cable connected to an oscilloscope (TDS 2024C, Tektronix, Beaverton, Oreg.) or the ground pin of the DAQ, through a piece of metal (contact area of 5 mm$^2$) touching the skin of the paw, and held stationary by a test clip whose spring had been stretched to make it weaker.

Two prototype systems have been implemented, tested, and verified: a custom-built system (FIGS. 3A-B-20) and a system (FIGS. 21-24) created by adapting and extending a commercially available device. Craniotomies are now automatically being made in the skulls of mice on a routine basis.

Figures 3A, 3B:
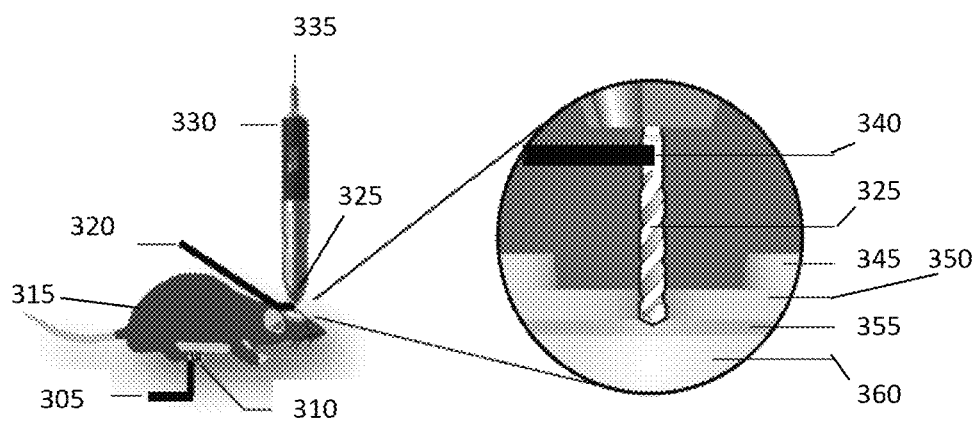
FIGS. 3A-B illustrate an example experimental setup suitable for use in performing the method.
Figure 20:
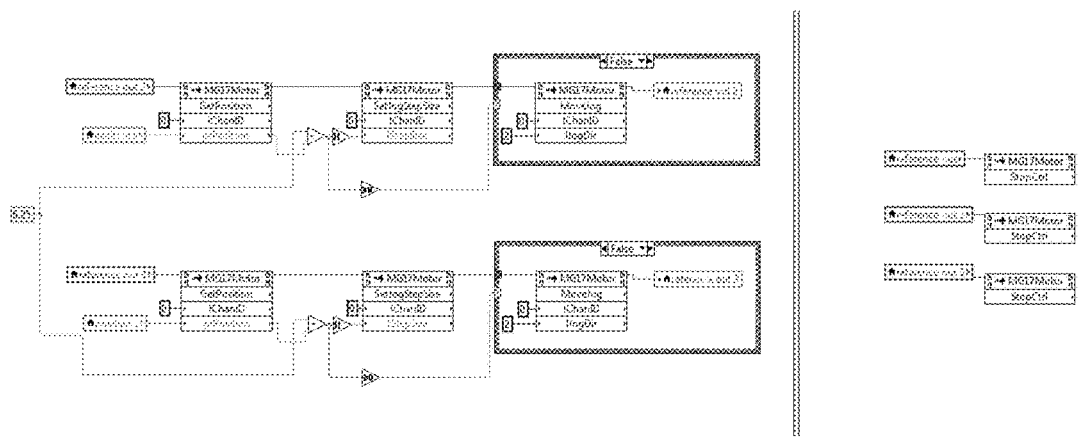

Custom-Built Embodiment (FIGS. 3A-B-20

A custom-built system was constructed that consists of an air-powered dental drill (PR-304, NSK, Tokyo, Japan) mounted on a three-axis computer-controlled stage equipped with three motors (PT3/M-Z8 stage, TDC001 controllers, TCH002 power supply, Thorlabs, Newton, N.J.), using a 3D-printed, electrically-insulating mount made of acrylonitrile butadiene styrene (ABS), with an electric potential detection circuit running through the drill bit. While an air-powered drill is described in conjunction with this embodiment, it will be clear to one of skill in the art that an electric drill, such as, but not limited to, an electrical micromotor carving tool is also suitable for use in the invention.

FIGS. 3A-B together are an illustration of an experimental setup suitable for use in performing the method. Shown in FIG. 3 are wire 305 attached to grounded paw 310 of mouse 315, wire 320 attached to drill bit 325 of drill 330 having air power input 335, electrical contact to bit 340, mouse skin 345, skull 350, fluid and meninges 355, and mouse brain 360.

While in the depicted embodiment the AC signal is sent through the drill bit and the ground is on the paw of the animal, it is also possible to send the signal through the paw and have the drill bit be the ground. This alternate arrangement provides a common ground with the drill so that the electrical noise can be lowered.

Although optional, it has been found that the best results are obtained by using head-fixed animals, with a metal plate being attached to the skull of the animal and held securely so that there is minimal detectable motion of the skull with respect to the drill.

Figure 4:
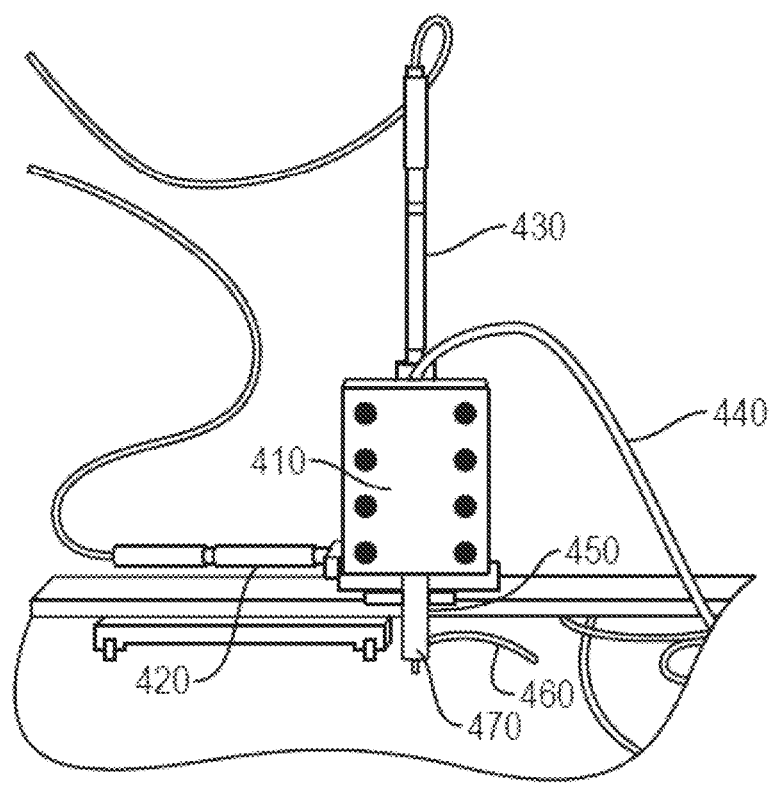

FIG. 4 depicts a custom-made autodrilling robot implemented according to one aspect of the invention. Shown in FIG. 4 are electrically insulating drill mount 410, horizontal motorized linear stage 420, vertical motorized linear stage 430, compressed air input 440 for air powered dental drill 450, and electrical contact 460 to drill bit 470.

The motors used with the motorized three-axis stage have a repeatable step size of 200 nm, a travel distance of 25 mm, and are controlled by the DAQ, driven with LabVIEW commands. Usually, step sizes of 5 μm in the z-direction were used, aiming for a resolution comparable to that of a cell diameter, so the motor precision used was probably more than what is needed. Thus, implementations that are several-fold cheaper than presented here might well be assembled; the motors in the example implementation were chosen to allow exploration of the parameters of autodrilling. A common lab air supply was used to power the dental drill, and a solenoid valve (EV-2-6, Clippard, Cincinnati, Ohio) was connected between the air supply and the dental drill so that the dental drill could be turned on and off through a digital signal from the same Lab VIEW program.

Figure 5:
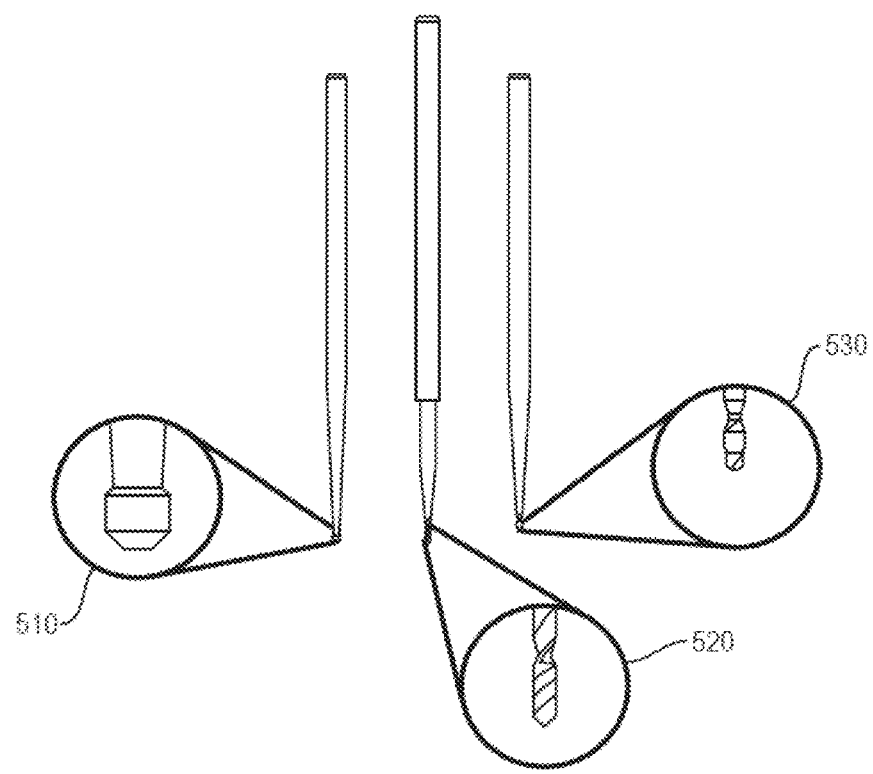

FIG. 5 depicts various drill bits found to be usable in the implementation of FIG. 4, including a commercially available dental burr 510, 500 μm in diameter, a custom drill bit 520 fusing a 200 μm tip with a custom aluminum dental drill adapter, and a custom 200 μm end mill 530 created by using a lathe to turn down a commercially available bit. Scale bar, 1/16". While specific drilling bits are pictured, it will be clear to one of skill in the art of the invention that suitable drill bits useable in the invention are not limited to the ones depicted in FIG. 5.

Dental drills are inexpensive and capable of extremely high rotary rates with minimal vibration, which is why they are popular in neuroscience for making small craniotomies. Most dental drills have a standard opening of 1/16" that fits commercially available dental burrs. These burrs range variously in size and shape, but are only available down to 500 μm in diameter. Commercially available drill bits come in sizes of 200 μm diameter and less (McMaster-Carr), but have a 1 mm diameter shank that is too small to fit into the dental drill. It was desirable to create very small craniotomies, so a custom adapter was built that bridged this 1 mm to 1/16" gap in order to use these drill bits. To produce these adapters, a lathe was used to first drill a 1 mm hole in a 1/4 in diameter aluminum rod. Next, this rod was turned down with the lathe to an outer diameter of 1/16" and cut to 25 mm in length. The drill bits were then cut down to about 10 mm in length using a grinding tool, and the drill bit was then press fit into the adapter. One idea explored was a custom-made chuck that would allow various diameter drill bits to be used with the dental drill. This idea was abandoned because it was found that the high speed of the dental drill (up to a nominal 320,000 rpm) requires a precisely balanced chuck to eliminate vibrations; the adapters produced in the example implementation are, in contrast, quite inexpensive (a few cents of material cost per adapter) and quick to produce (~15 minutes each). However, it is clear that use and/or creation of a chuck or any of the many other types of adaptors known in the art is within the skill of the artisan and therefore within the scope of the invention.

The drill bits used in the example implementation have a diameter of 200 μm and a point angle of 118°. This angled cutting edge means that, for a fully bored hole in the skull, the drill bit must penetrate 60 μm beyond the inner surface of the skull, increasing the risk of damage. This is an issue with all pointed drill bits used in neuroscience, not just those being used with dental drills.

Miniature square end mills (Harvey Tools) could result in more consistent craniotomy openings, but are not typically used in neuroscience applications. End mills with a 200 μm diameter and ⅛" shank were turned down by a machine shop in order to be able to fit into the 1/16" dental drill opening. Since these have a flat end, a fully bored out craniotomy is created when the circuit detects breakthrough of the skull. For the same reason, these are potentially less damaging to the brain as well: since they are not pointed, they do not need to extend beyond the base of the skull to complete full craniotomy. End mills also allow for cutting in all three directions so more elaborate craniotomies can be created.

Calibrating the stereotaxic coordinates can be performed by moving the drill tip to bregma or lambda for a well-aligned mouse in a stereotaxic frame, and then zeroing the coordinates in the software. Use of a head-fixed mouse was found to produce the best results.

In the original custom-built system, accurate measurements of drill-to-body potential could not be made while the drill bit was spinning, presumably due to poor electrical contact between a spinning bit and its surroundings. Therefore, the drill was always turned off, waiting for the drill to stop spinning, before taking a measurement of the drill-to-body electrical potential. This problem was solved in a subsequent implementation, which employs a ball bearing installed on the drill bit to which the signal wire is attached, allowing continuous impedance testing without the need to stop the drill. The inside of the bearing is filled with conductive grease, in order to create electrical continuity between the drill bit and the signal wire.

Figure 6A:
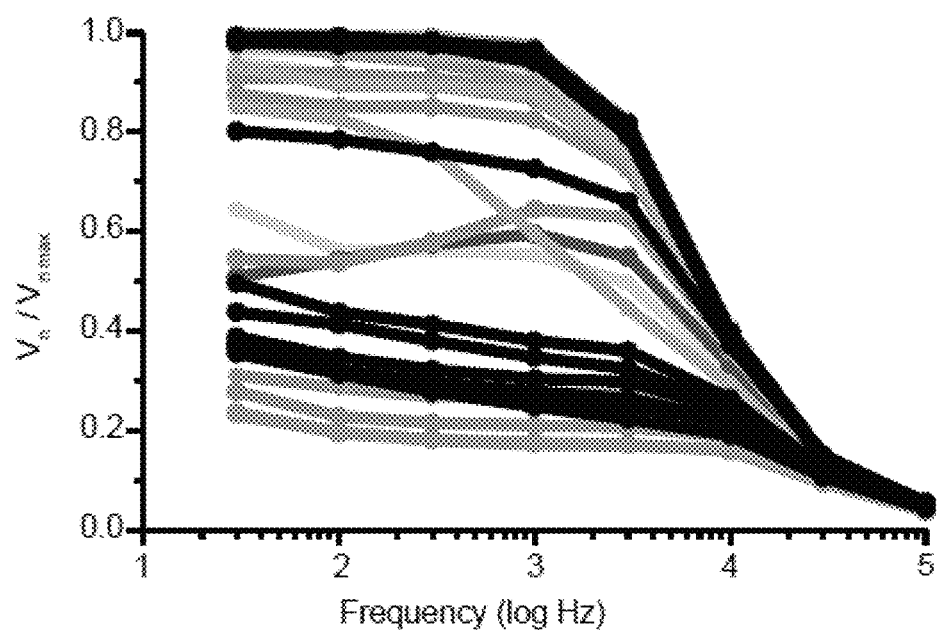
Figure 6B:
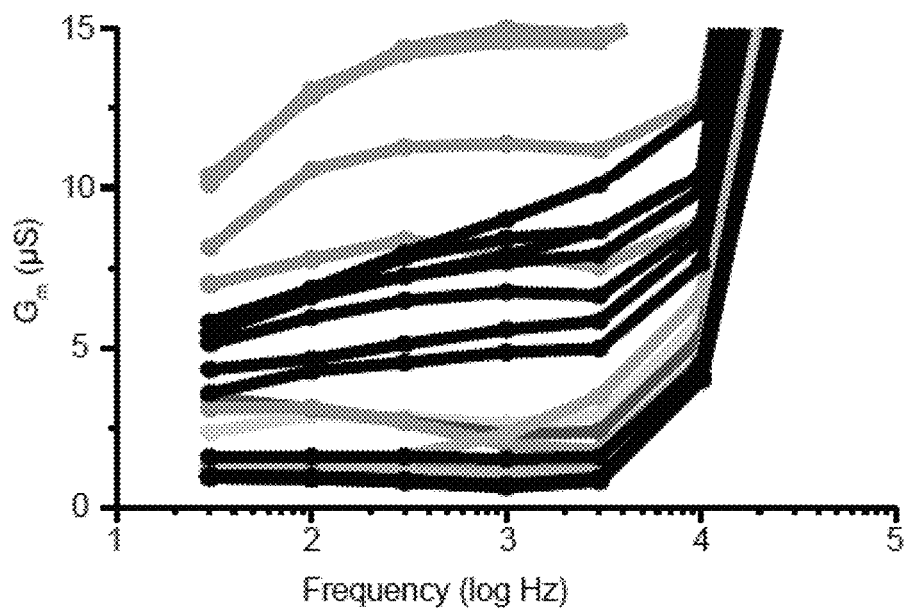
FIG. 6B is a graph of electrical conductance vs. frequency for the experiment of FIG. 6A.

FIG. 6A is a graph of normalized electric potential across the drill (as in FIG. 3, but with the electrical contact on the bit moved to touch the drill itself) and mouse, as a function of frequency, as a 500 μm dental burr is lowered into the skull for 7 different mice (step size, 10 μm for six mice, 50 μm for the seventh. FIG. 6B is a graph of electrical conductance vs. frequency (as in FIG. 6A) for all 7 mice of FIG. 6A. The data in FIGS. 6A-B was obtained using a function generator (33250A, Agilent, at 20V, varying frequencies) through a sense resistor (681 kW) and a wire in contact with the drill body. A coaxial cable conducted the electrical signal from the function generator to the drill and from the mouse back to the oscilloscope (TDS 2024C, Tektronix, Beaverton, Oreg.). The oscilloscope was used to measure the voltage drop, $V_n$, across the mouse. This method generally only works when the signal amplitude is much higher than the noise, which is the case when there is a large driving current.

Measurements of the voltage drop with a ground electrode consisting of a skull screw (self-tapping screw, size 000 thread, #303 stainless steel, 3/32" length, J. J. Morris Company, Southbridge, Mass.) inserted into a manually drilled craniotomy showed no improvement in the ability to detect a craniotomy opening by the robot drilling at a second site, presumably because the conductance through the body and through the brain are both high compared to the conductance of the skull.

The voltage drop across the sense resistor (see FIG. 2) is $V_s = V_{in} - V_n$, and the current flow through the sense resistor is $i_s = V_s / R_s$. If parasitic currents, defined as $i_p = V_n / Z_p$, are present, e.g., via capacitive coupling of signal wires with grounded shielding in a cable, then some of the sense current flows through a parasitic impedance $Z_p$, calculated as the ratio of $V_p / i_s$ (measured when the mouse is not there). The current flow through the mouse, when present, is $i_m = i_s - i_p$.

From these equations, the ratio of the voltage drop across the mouse to that of the input voltage, $V_n / V_{in}$, is calculated as $V_n / V_{in} = 1 - R_s (Z_p + Z_m) / (R_s (Z_p + Z_m) + Z_p Z_m)$. When the drill tip makes a hole in the skull, it was found that $Z_m$ decreases by five orders of magnitude, and this ratio decreases by about two orders of magnitude given a sense resistance of 10 MΩ.

To facilitate comparison across the multiple experimental setups explored, e.g., different cables and different input voltages, the voltage was normalized across the mouse, $V_n$, by the maximum recorded voltage, $V_{n\ max}$, recorded in the open loop configuration with no mouse in the circuit, before drilling began. The maximum recorded voltage is equal to the input voltage, when twisted pairs are used, or less for the case of parasitic currents, which occur with the coaxial and USB cables.

For FIGS. 6A-B, the impedance of the drill was included in the circuit because the simplest method for sending a signal through the drill is to connect a wire to the body of the drill, which is conductive to the drill bit. This impedance would show up as a resistor in series with the mouse (as in FIG. 2). Electric potential measurements were made in discrete steps. For FIGS. 6A-B, the drill was turned, a step of 10 μm or 50 μm was taken, the drill was turned off and a measurement was made after the drill came to a complete stop.

FIGS. 7-10A-B depict implementation aspects of the method for autodrilling, and validation of thereof, when run on the robot of FIGS. 2-5.

Electrical Current. For the experiments of FIGS. 7-10A-B, the 1 mV amplitude and 10 MΩ sense resistor were chosen so that the maximum possible electrical current through the mouse (equal to the amplitude of the injected sine wave divided by the sense resistance) was small (~100 pA), in order to avoid brain stimulation. Using the cross-sectional area of a 200 μm diameter cylinder as the electrode area of the drill bit, the current density was approximately 0.0032 A/m², nearly two orders of magnitude less than the lowest current densities (0.28 A/m²) capable of stimulating brain tissue [Brunoni A. R., Nitsche M. A., Bolognini N., Bikson M., Wagner T., Merabet L., Edwards D. J., Valero-Cabre A., Rotenberg A., Pascual-Leone A., Ferrucci R., Priori A., Boggio P. S., Fregni F. Clinical research with transcranial direct current stimulation (tDCS): challenges and future directions. Brain Stimul. 5(3): 175-195, 2012; Nitsche M. A., Liebetanz D., Lang N., Antal A., Tergau F., Paulus. Safety criteria for transcranial direct current stimulation (tDCS) in humans. Clin Neurophysiol. 114(11): 2220-2222, 2003; Chaieb L., Antal A., Paulus W. Transcranial alternating current stimulation in the low kHz range increases motor cortex excitability. Restor Neurol Neurosci. 29(3): 167-175, 2011]. Furthermore, this current was only applied across the brain for a few seconds during the drilling operation. Additionally, the signal processing methods used above could in principle be used to lower the current down further, if desired.

The circuit used to produce the data of FIGS. 8A-B and 10A-B works by sending a sine wave from a LabVIEW (LabVIEW 2011, National Instruments, Austin, Tex.) data acquisition board (DAQ) (NI USB-6353, National Instruments, Austin, Tex.) (1 mV, 100 Hz), through a sense resistor (10 MW) and a wire directly in contact with the drill bit. The cable conducts the electrical signal from the DAQ to the drill and from the mouse back to the DAQ. This cable consisted of a shielded USB cable. The wire mesh shields of the USB cable was connected to earth ground to minimize the effects of environmental noise. The rear paw of the mouse made electrical contact to the ground lead of this cable connected to the ground pin of the DAQ, through a piece of metal (contact area of 5 mm²) touching the skin of the paw, and held stationary by a test clip whose spring had been stretched to make it weaker.

The DAQ measures $V_n$ in a different manner than for the prior embodiment. The LabVIEW program performs a partial discrete Fourier transform on $V_n$, calculating the amplitude of $V_n$ as sqrt(Re(X)²+Im(X)²)/N, where N=15,000 is the number of samples read, and X is the coefficient of the sinusoidal component of the measured samples at the test frequency (100 Hz). X is defined as $X=\Sigma_{n=0}^{N-1} x_n e^{-i2\pi kn/N}$ where $x_n$ is the $n^{th}$ measurement, and k is calculated as N/(sampling rate (25 KHz) divided by the input frequency), which equates to the number of cycles that are recorded (in this case 60). Re(X) is calculated as $\Sigma_{n=1}^{N-1} x_n \cos(-2\pi kn/N)$, and Im(X) is calculated as $\Sigma_{n=1}^{N-1} x_n \sin(-2\pi kn/N)$. This method of measuring $V_n$ was chosen because the driving current of about 100 pA is deliberately very small, in order to avoid any biological effects, which also makes it smaller than the noise (when examined by eye).

The impedance of the drill was removed from the circuit by having a wire touch the shank of the drill bit directly, taking care not to apply excessive radial forces to the bit which could cause premature wear of the bearings. Electric potential measurements were made in discrete steps. The solenoid valve was turned on for 300 µs, a step of 5 µm was taken, a pause of 3.5 s allowed the drill to come to a complete stop, and then a measurement was taken for 0.6 s.

Once a threshold was defined that balanced craniotomy success and safety, the method of FIG. 1 was implemented in order to perform electric potential measurements over time while a drill was lowered through the skull in 5 µm steps, halting motion when the drill-to-body potential dropped below the threshold. Since each drill step and measurement step took about 4 seconds, each craniotomy took about four minutes.

Figure 7:
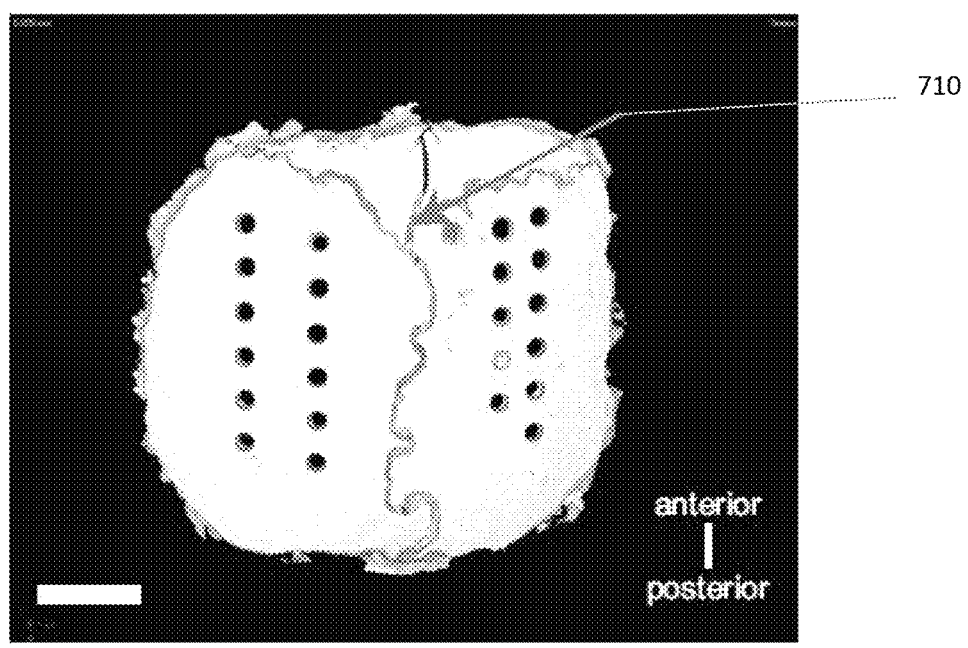
Figure 9:
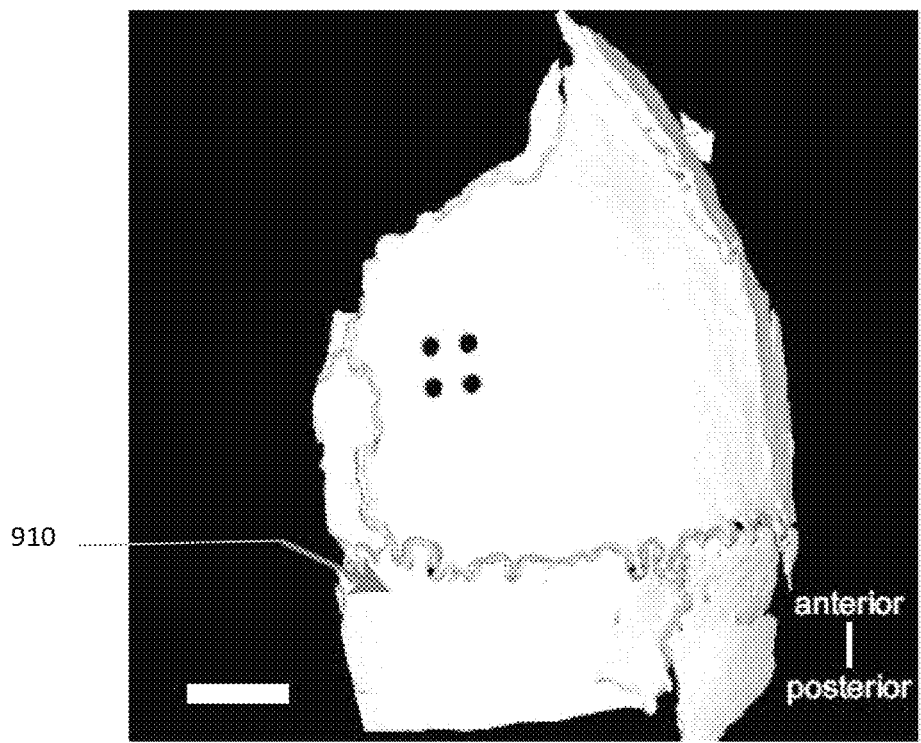

Across multiple trials of the custom craniotomy robot and method, it was found that craniotomies could be reliably drilled using the normalized electric potential threshold of 0.65 (FIGS. 7, 9; n=72 craniotomies in 3 mice). For 6 of the craniotomies, bleeding was observed from the skull after drilling to only a shallow depth (implying again that a blood vessel in the skull had been hit). For 4 of these cases, waiting ~10-20 minutes for the vessel to clot was sufficient to allow the procedure to continue to the point of a complete craniotomy.

Figure 8A:
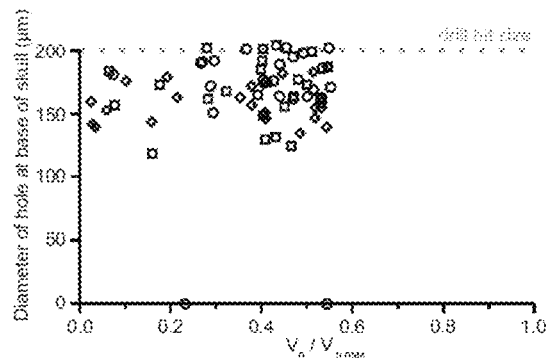
FIG. 8A is a plot of craniotomy hole size as a function of final stopping normalized electric potential using the drilling pattern of FIG. 7 and the custom-made automated craniotomy robot.
Figure 8B:
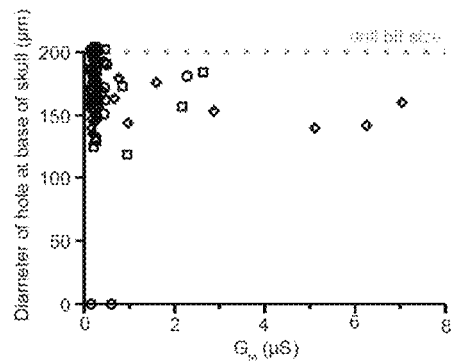
FIG. 8B is a plot of craniotomy hole size vs. electrical conductance, for the data of FIG. 8A.

FIG. 7 is a representative CT scan of a skull, showing the bregma 710 and exhibiting the experimental drilling pattern used to produce the data of FIGS. 8A-B. Scale bar is 1 mm. FIG. 8A is a plot of craniotomy hole size as a function of final stopping normalized electric potential for 72 craniotomies in 3 mice with a 200 µm drill bit, using the drilling pattern of FIG. 7 and the custom-made automated craniotomy robot with a step size of 5 µm and normalized electrical potential threshold of 0.65. Each mouse is represented by a different shape. For 2 of the 72 craniotomies, the drill bit did not pass the bottom of the skull, and thus are at the y=0 line. FIG. 8B is a plot of craniotomy hole size vs. electrical conductance for the data of FIG. 8A.

Figure 10A:
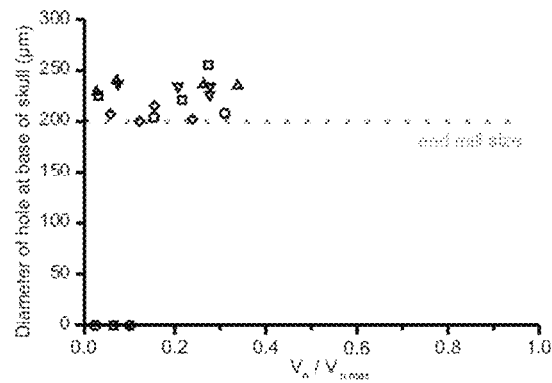
Figure 10B:
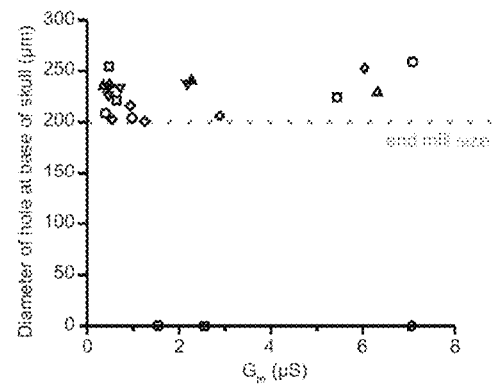
FIG. 10B is a plot of electrical conductance vs. craniotomy hole size, for the data of FIG. 10A.

FIG. 9 is a representative CT scan of another skull, showing the lambda 910 and exhibiting an experimental drilling pattern used to produce the data of FIGS. 10A-B. Scale bar is 1 mm. FIG. 10A is a plot of hole size as a function of final stopping normalized electric potential for 20 craniotomies in 5 mice with a 200 µm flat-end end mill, using the drilling pattern of FIG. 9 and the custom-made automated craniotomy robot with a step size of 5 µm and normalized electrical potential threshold of 0.45. Each mouse is represented by a different shape. For 3 of the 20 craniotomies, the drill bit did not pass the bottom of the skull, and thus are at the y=0 line. FIG. 10B (3G) is a plot of electrical conductance vs. hole size for the data of FIG. 10A.

The holes drilled in FIGS. 7 and 9 were typically less than the width of the drill bit, because the pointed tip would break through before the wider shaft, resulting in a not-completely bored out hole. As noted earlier, the use of a pointed or rounded drill bit, although popular in neuroscience, may also result in part of the drill projecting significantly below the skull base, potentially injuring the brain. Blunt-tipped end mills of 200 mm diameter were created that could be used in a dental drill, and the threshold used was changed to a lower value, 0.45. It was found that cylindrical holes could now be made, with diameters equal to or larger than the end mill diameter (n=20 craniotomies in 5 mice). For 3 of the 20 craniotomies, skull bleeding was observed; in principle these could have been allowed to continue, after a waiting period to allow clotting. Craniotomy sizes of greater than 200 µm were due to some end mills not being perfectly concentrically machined down, in the machining process used to modify the end mills.

For the end mill experiments, the precision of the craniotomy robot was characterized. Four craniotomies in an array were created, with 500 µm spacing (center-to-center) in both the anteroposterior and mediolateral directions. The measured center-to-center distance was 496±6 µm (mean±std. dev., n=10 pairs of craniotomies, including the partial craniotomies) in the mediolateral direction, and 492±10 µm in the anteroposterior direction. These errors approach the resolution of the CT scanner used to image the skulls (~5 µm).

The two steps in this procedure that required manual intervention were the initial alignment of the drill bit with the center of the desired window, and the removal of the circular bone fragment under saline. In between these steps, the robot operated independently. In some instances, the drill passed through a skull vessel, causing bleeding that quickly subsided. In no cases was damage to the vessels of the meninges or the brain itself observed.

Design, construction, and operation of a "custom-built" automated craniotomy robot.

In one particular implementation, an automated craniotomy robot consists of a voltage detection circuit, a drill, and actuators. Table 1 is an example parts list for an embodiment of a custom-built implementation of the present invention.

TABLE 1

| Description | Vendor | Model # |
| --- | --- | --- |
| air powered dental drill | NSK | PR-304 |
| DAQ | National Instruments | NI USB 6353 |
| solenoid valves | Clippard | EV-2-6 |
| xyz stage + motors | Thor Labs | PT3/M-Z8 |
| motor controller | Thor Labs | TDC001 |
| motor controller power supply | Thor Labs | TCH002 |
| 200 µm drill bit | McMaster | 8904A27 |
| 200 µm end mill | Harvey Tool | 13908 |
| drill holder | custom | |
| stereotaxic | Kopf | 900 |
| 10 MΩ resistor | various | |
| shielded USB cable | various | |

The data acquisition board (DAQ board Model: NI USB-6353) is used to interact with LabVIEW software. Specifically, an analog output is used to generate the AC signal for the detection circuit. An analog input is used to measure this signal, and a digital output is used to turn the drill on and off with a solenoid valve.

The sense resistor (10 MΩ) is connected directly on the DAQ board to minimize noise. The sense resistor is large so that the maximum current remains low.

A shielded USB cable is used to send the AC signal to and from the mouse. Without a shielded cable, environmental noise would dominate the signal since a very small amount of current HO pA) is used in the detection circuit. The ground of the USB cable is connected to earth ground.

Figure 11:
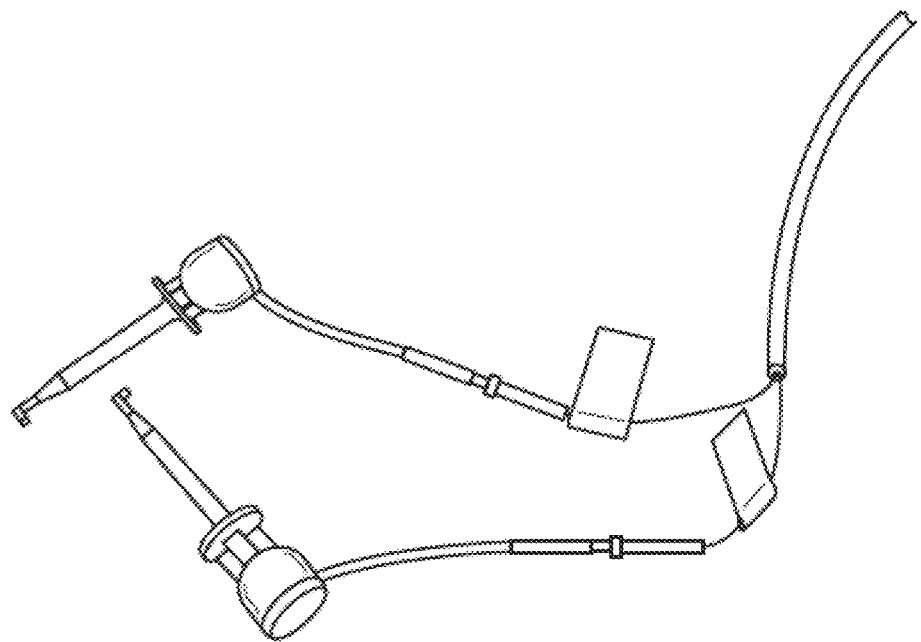

As shown in FIG. 11, minigrabbers are used to connect to the drill and to the body of the animal. These have been modified to decrease their applied force by stretching their springs. The unshielded wire distance is minimized for noise purposes.

In a preferred embodiment, an air-powered dental drill (NSK Presto) that has the drill axis aligned with the body of the dental drill is employed. Unlike most dental drills that have a 90° bend between the handle and the drill axis, this drill does not get in the way of the stereotaxic frame. It will be clear to one of skill in the art that there are other dental drills that would be suitable for use in the invention, as well as other types of drills. The NSK Presto dental drill was selected because it has almost no run-out, unlike the first dental drill that was tried (Buffalo No. 220).

The electrically insulated dental drill holder is a custom 3D printed part that secures the dental drill to the three-axis stage. It is made of plastic (ABS), which prevents the detection signal from travelling through the stage. This part was initially designed for the first dental drill tried, but can also secure the NSK Presto. It is clear that it is within the skill of the artisan to create a custom holder for whatever drill is selected for use in the invention.

A three-axis stage with linear servomotors (Model: PT3-Z8) has 1" of travel in each direction. These motors have a repeatable step size of 0.2 μm. The program steps down in 5 μm steps so this level of resolution is most likely unnecessary. These motors are also controllable through LabVIEW.

Power supply for motors (e.g. TPS001, TPS008, TCH002). Each motor controller needs to receive power and send/receive signals from the computer. The cheapest option found was an individual power supply for each motor controller. In this case, each motor controller will also have to be connected to the computer through a USB cable. The medium cost option is a single power supply for up to eight motor controllers. In this option, each motor controller still needs to be connected to the computer through a USB cable. Another suitable alternate option is a power supply and base for up to six motor controllers. The base connects all of the motor controllers to the computer through a single USB cable. While specific motor configurations are described, any of the many motors and motor configurations known in the art would be suitable for use in the invention.

A stereotaxic (Kopf Model 900) is used to secure the animal during surgery, as in a normal surgery setup. Unlike some other models, the Kopf Model 900 has a lot of space for the drill to fit, but other sterotaxics, and other methods of securing the animal, would also be suitable.

A solenoid valve (such as, but not limited to, Clippard EV-2-6) is used to turn the dental drill on and off through computer commands.

Since the DAQ typically cannot provide enough current to activate the solenoid valve, a transistor and DC power supply may also be required when using a DAQ.

Commercially available dental burrs come in various shapes and sizes but only go down to 500 μm in diameter. Miniature drill bits and end mills (200 μm drill bit from McMaster 8904A27; 200 μm flat end mill from Harvey Tool 13908) are used to create craniotomies of 200 μm diameter (both the drill bits and end mills come in various sizes, starting at 50 μm in diameter). Since dental drills currently come with a standard chuck size that will only accept 1/16" diameter shanks, and these drill bits have 1 mm shanks, custom aluminum sleeves with a 1 mm ID and a 1/16" OD are machined. The end mills come with a 1/8" shank. These bits are ground down. This should be done with special tooling since the bits are made of tungsten carbide, and it is very important that the concentricity of the bit shank and cutting surfaces is maintained when the shank diameter is reduced. Also, a wire is required to make direct contact with the drill bit for the detection circuit.

Other parts used for the prototype implementation include, but are not limited to, a computer with LabVIEW software, wall air supply, standard surgery equipment, a secure mount for 3-axis stage, and stereomicroscope LabVIEW Program Description/Walkthrough. Before running the program, the user inputs how many craniotomies are to be drilled by entering the number of rows and columns. Also, the spacing between craniotomies in the rows and columns is entered. Finally, a file path for a data log is entered if it is desired. The data log creates a text file for each craniotomy that indicates the voltage amplitude at each drill depth.

Figure 12:
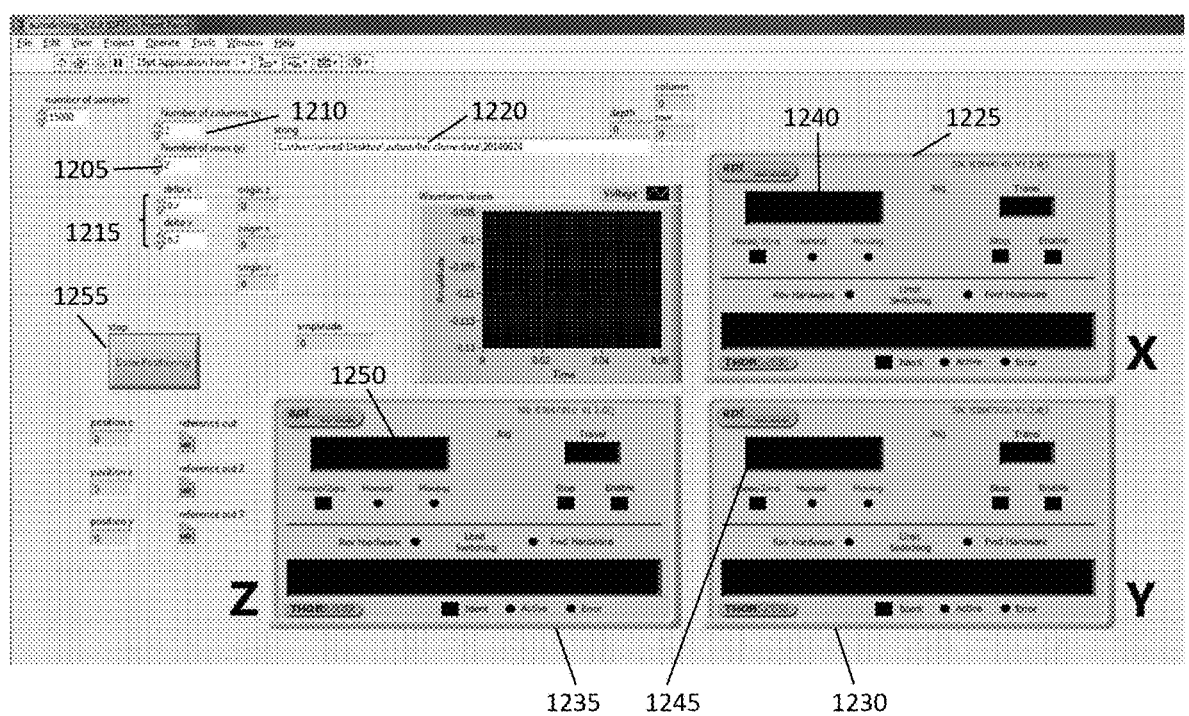

FIG. 12 depicts the front panel of the LabVIEW control screen used in the prototype implementation. Here, the user enters the number of rows 1205 and columns 1210, and the spacing 1215 between each craniotomy. Also, the user enters where 1220 the data file will be stored.

When the program is started, it takes a few seconds for the motors to initialize. After they are initialized, they can be moved into position by using the buttons on the motor drivers or by entering a number for the displacement of each motor in the LabVIEW window.

The screen also includes interfaces 1225, 1230, 1235 for the servomotors. When the servomotors are initiated, the fields are filled in with numbers. After initialization, numbers can be entered to specify the location of the motors in fields 1240, 1245, 1250.

Once the drill is positioned in the location for the first craniotomy, the user presses the "Done Positioning" button 1255 and the automated craniotomy robot begins drilling the first hole. It will proceed to drill all the holes, and when it finishes, it will retract the drill to the maximum height and center the other two axes to prepare for the next procedure.

FIGS. 13-20 are schematic flowcharts and diagrams relating to the operation of the example implementation of the custom-built system according to the invention. The LabVIEW visual interface is based on a flat sequence structure, so that it operates in a linear manner where each frame of the program executes one after the other, from left to right.

Figure 13:
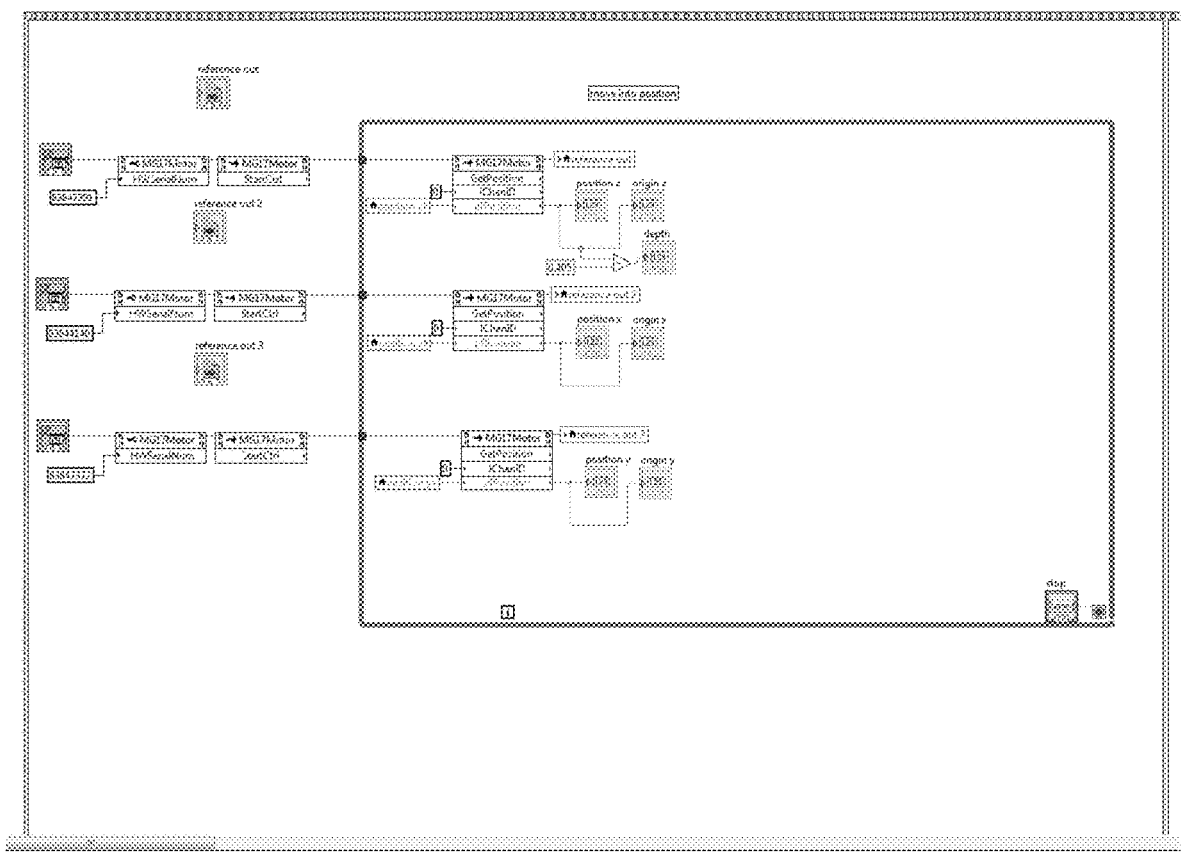

FIG. 13 is a schematic flowchart depicting the steps by which the system initializes the motors and then waits for the user to position the drill in the correct location. The blocks labeled "MG17MOTOR" are used to interface with the motors. First, the motors are sent a serial number that corresponds to each different motor. Next, they receive a start command. The final motor block in this frame is the "GetPosition" block. This gets the position of each motor and stores it in two local variables: position and origin. Since these motor blocks are in a while loop, as the user moves the motors the position is constantly being updated. Only after the "Done Positioning" button is pushed, do the position values get stored in the two previously mentioned local variables. Another item to note is the reference out local variables. These are used throughout the program whenever a "MG17MOTOR" block is used. These store information that the motor controllers need so it is important that they are passed between the different motor blocks.

Figure 14A:
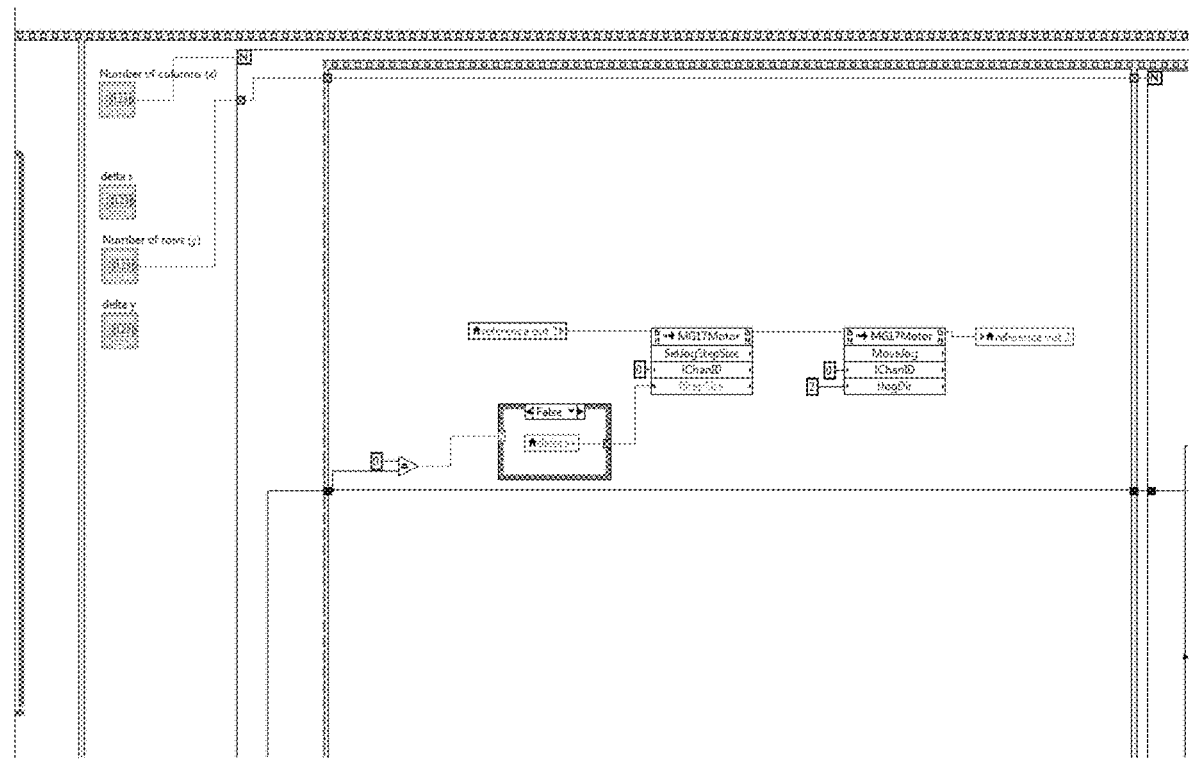
FIGS. 14A and 14B are schematic flowcharts depicting the steps by which the example system moves the drill into position and prepares to drill.

FIG. 14A is a schematic flowchart depicting the steps by which the system moves the drill into position and prepares to perform the drilling. There are several nested loops that move the drill to each position and automatically drill down through the skull. The outermost loop is a loop that does the columns, or x-coordinates for the craniotomies. As seen in FIG. 14A, it moves the x motor the distance "delta x," unless it is the first column. If it is the first column, the conditional statement tells the motor to move a step size of zero since the drill is already in the desired location for the first column of craniotomies. The "MoveJog" command is used for the first time here. This gets an input of either 1 or 2 for the direction (in this case a 2).

Figure 14B:
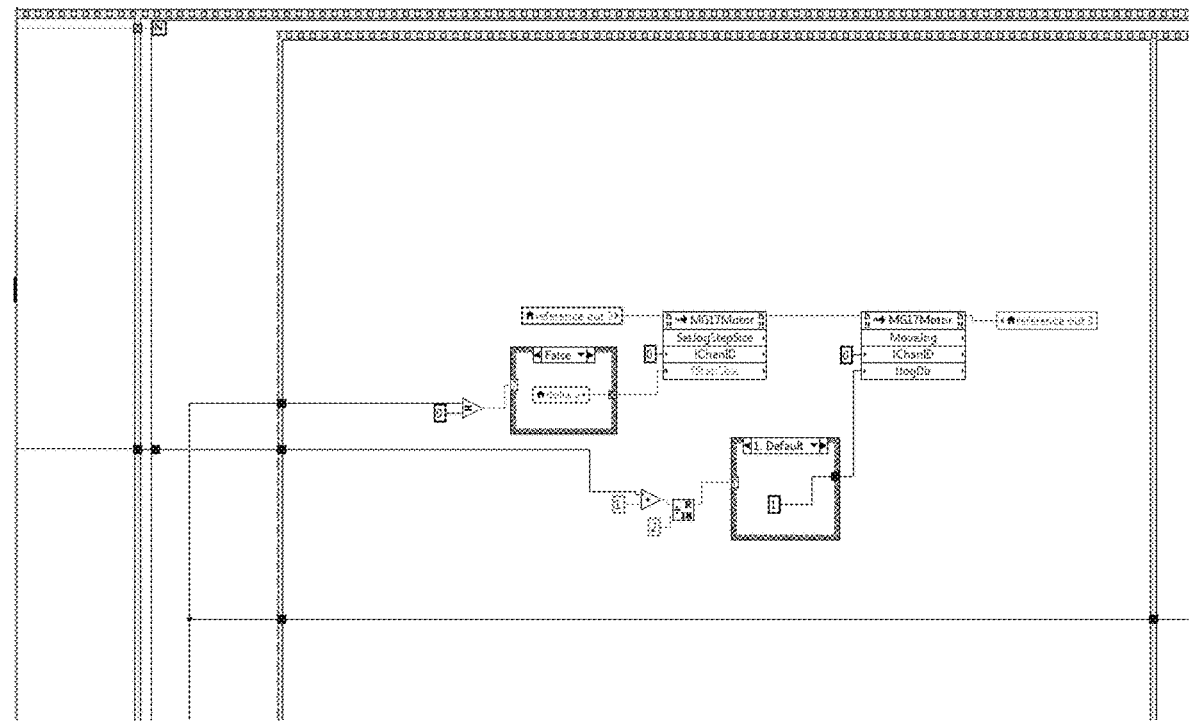

After the drill is moved to the column location, it is next moved to the row location, as seen in FIG. 14B. As before, if it is the first row, the motor does not move, since the drill is already in the correct location. Otherwise, the drill moves over the distance "delta y." Additionally, instead of moving in the same direction each time, the y motor changes direction for each column.

Figure 15:

For efficiency, in a preferred embodiment, the drill moves in the pattern depicted in FIG. 15. This saves a small amount of drilling time because the skull curvature in the x-direction is greater than that in the y-direction. A greater curvature in the x-direction means that the drill must be retracted a large distance in order to safely move in the x-direction without hitting the skull. Retracting the drill more means that the drill may have to take more steps before creating a craniotomy, which leads to a longer drilling time. By moving the robot as in FIG. 15, a smaller z offset is used between the craniotomies in the y direction. This is just a minor optional feature, but does save some time, especially for large numbers of craniotomies.

Figure 16:
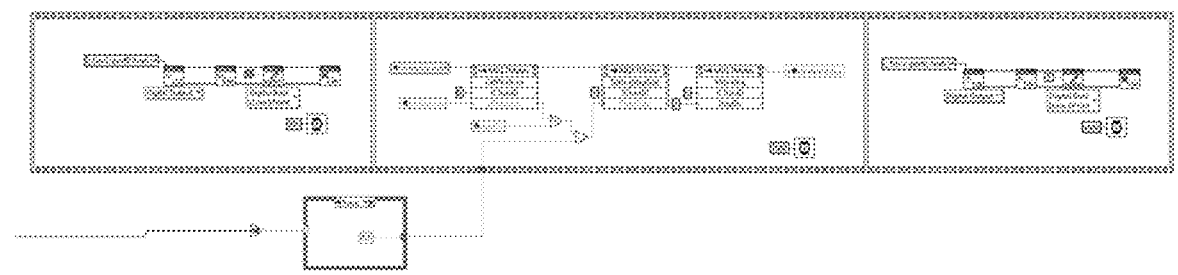

FIG. 16 is a schematic flowchart of another optional procedure used to try to save some drilling time. After a craniotomy is made, the depth at which the drill stopped is recorded and the next craniotomy is drilled to this depth plus an offset of either 300 or 400 µm. The skull is only about 150 µm thick, but due to the curvature of the skull, a 300-400 µm offset is required to ensure that the drill does not go too far on this step. For this step, a digital on signal is sent to activate the drill, then the z motor moves the drill down, and finally the drill is turned off. There are pauses in each of the frames in this sequence to ensure that each step is finished before the next one starts.

Figure 17A:
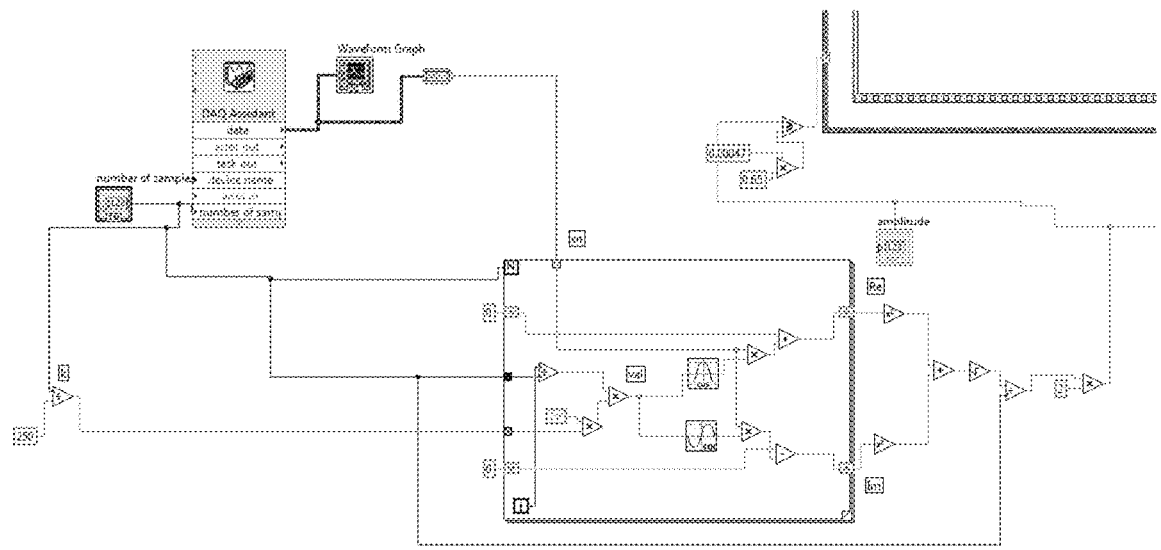
FIGS. 17A and 17B are schematic flowcharts depicting the steps by which the example system performs the automated drilling.
Figure 17B:
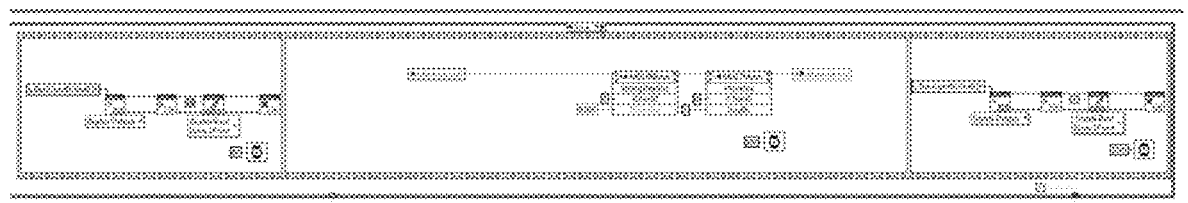

FIGS. 17A and 17B are schematic flowcharts depicting the steps by which the system actually performs the automated drilling. As shown in FIG. 17A, the first thing that happens is a measurement of the voltage amplitude is made. This is done using a discrete Fourier transform, which allows the detection signal to be a very low current signal by extracting the information from a noisy signal. The "for" loop in FIG. 17A is executing the discrete Fourier transform. The voltage amplitude obtained from this is compared to the threshold value, and this is used to make a decision in the next step. As shown in FIG. 17B, if the measured amplitude is greater than or equal to the threshold, this means that the increase in conductance associated with breaking through the skull has not occurred, and the robot must drill further. This sequence is similar to the one previously mentioned. The drill is turned on, the z motor moves down 5 µm, and then the drill is turned off.

Figure 18A:
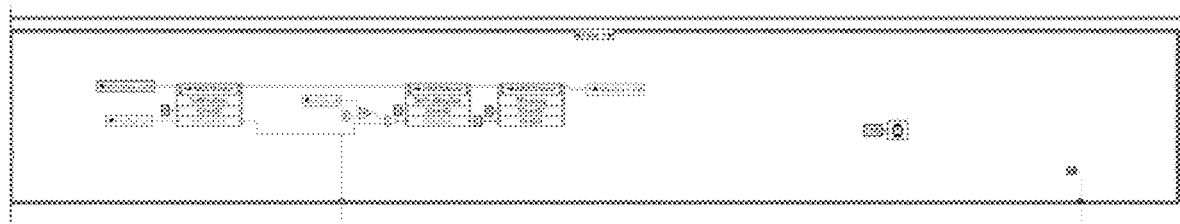
FIGS. 18A and 18B are schematic flowcharts depicting the steps by which the example system determines whether or not drilling should be performed.
Figure 18B:
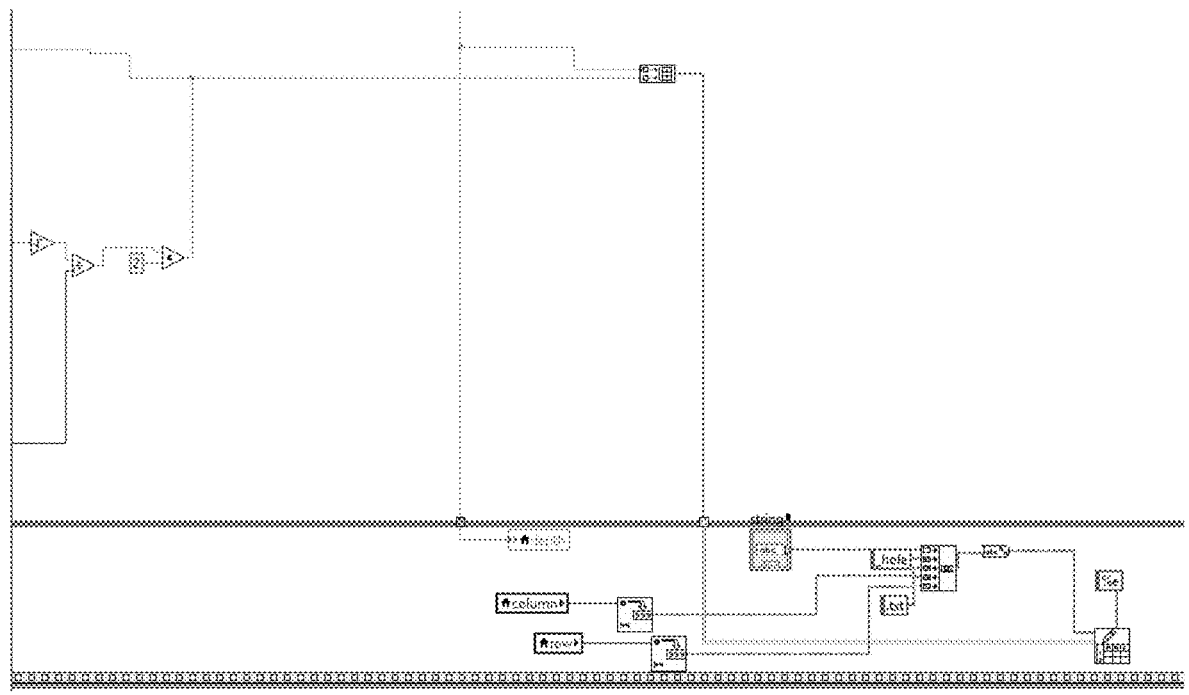

FIGS. 18A-B are schematic flowcharts depicting the steps by which the system determines whether or not drilling should be performed. As seen in FIG. 18A, if the measured voltage amplitude is below the threshold, the drill is not turned on, and the z motor retracts to a safe distance above the skull to move the drill to the next position. This stops the "while" loop that contains the amplitude measurement and drilling sequence, and allows the program to move to the next drilling position. As seen in FIG. 18B, each time a voltage amplitude measurement is made, it is recorded along with the depth at which it was made, including saving the depth location of the finished craniotomy when the voltage amplitude is below the threshold. This is stored in a .txt file.

Figure 19:
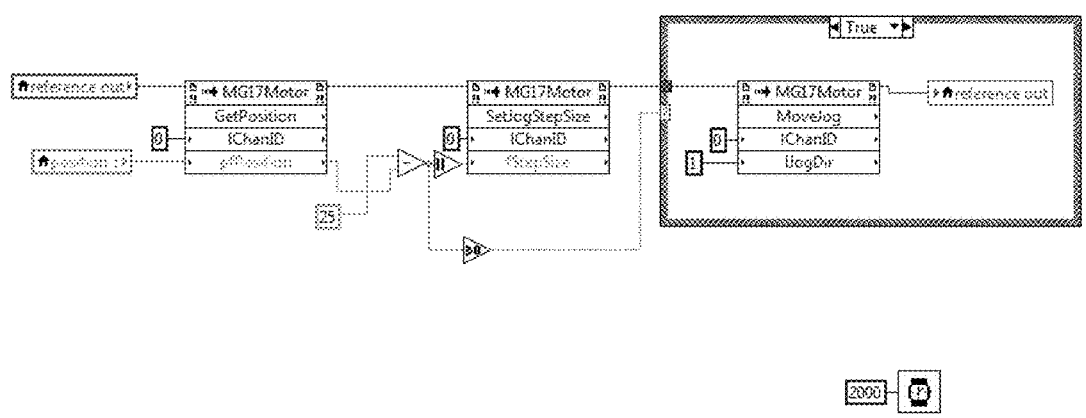

FIGS. 19 and 20 are schematic flowcharts depicting the steps by which the system retracts the drill and completes the program. After all the craniotomies have been made, the drill is retracted in the z-direction up to the maximum distance (FIG. 19). Then, the x and y motors are centered (FIG. 20). Finally, all three motors are stopped. This completes the automated craniotomy program.

Modified Commercial System Implementation (FIGS. 21-24)

To maximize the utility of the design, whether a commercially available craniotomy robot that normally operates in open-loop mode could also be modified to utilize this closed-loop method was explored. In one embodiment, the invention was implemented using a modified version of a commercially available motorized stereotaxic apparatus, a NeuroStar (Tubingen, Germany) stereotaxic robot. The NeuroStar was modified and found to be capable of creating reliable, clean craniotomies using the same conductance-based feedback method.

Figure 21:
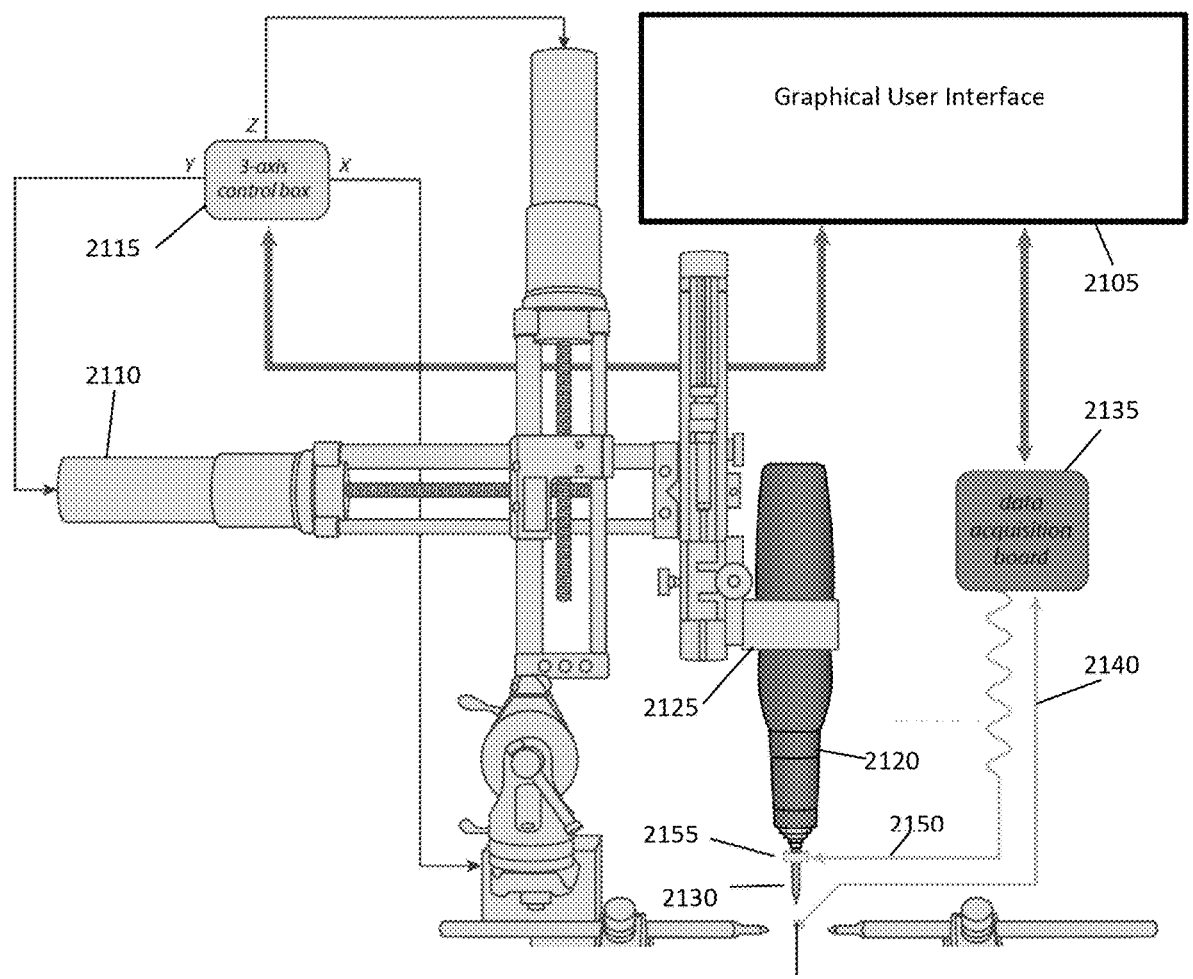

FIG. 21 is a schematic of an example implementation of a system for performing automated craniotomies utilizing a modification of the NeuroStar motorized stereotaxic, according to one exemplary implementation of the invention. As shown in FIG. 21, a graphical user interface (GUI) 2105 controls the movement of stereotaxic frame 2110 via 3-axis control box 2115. Micromotor carving drill 2120 with adjustable rotation speeds up to 45,000 RPM is attached to stereotaxic 2110 via custom adapter 2125. Drill 2120 turns end mill 2130 with a tip diameter of 200 µm. When the end mill breaks through the skull, it completes the circuit formed between a wire carrying the 100 Hz test signal from data acquisition board 2135 and test lead 2140 connected to the animal 2145. Signal wire 2150 is attached to drill bit 2130 via ball bearing 2155, allowing continuous impedance testing without the need to stop the drill.

The NeuroStar contains three separate stepper motors, one for each axis of movement in a standard sterotaxic frame. These motors are attached to a Kopf Model 900 Small Animal Stereotaxic Instrument (David Kopf Instruments, Tujunga, Calif.). Each motor is connected to a control unit, which is in turn connected via a USB interface to a computer.

The stepper motors operate by rotating the shaft of the Kopf stereotaxic positioner to drive movement along that axis, much in the same way an operator would use the same manual stereotaxic frame. The standard deviation of the specified steps was measured and found to be 1.8 µm for the rostral-caudal (X) axis, 2.0 µm for the medial-lateral (Y)

axis, and 1.2 µm for the dorsal-ventral (Z) axis. The range of travel along each axis is 70 mm, which is slightly more limited than that of the Kopf frame, to protect the motors from damage.

As purchased, the NeuroStar robot was only capable of operating in "open-loop" mode, so it was modified to respond to changes in conductance at the drill tip. In one implementation, the NeuroStar drill was replaced with an electrical micromotor carving tool (Ram Products, Inc., East Brunswick, N.J.) capable of achieving higher rotation speeds (up to 45,000 RPM) and accommodating square end mills with shank diameters of 1/8", as well as 1/16" drill bits with adapters. This alleviated the need to modify the end mills, but did require a custom adapter for attaching the drill to the stereotaxic frame. Unlike the default NeuroStar drill, this drill must be controlled manually (i.e., it cannot be stopped and started by the existing software).

Electric potential measurements were taken with a National Instruments data acquisition board at a rate of 2 Hz, with each measurement lasting 100 ms. The drill was moved down in 5 µm increments after every other measurement. If power at 100 Hz (based on the fast Fourier transform of the incoming signal) exceeded a threshold of 0.01 $V^2$, the drill was retracted to its starting position. Sending the test signal through a ball bearing made it possible to take measurements without stopping the drill, speeding up the drilling process substantially.

The drill bit (a 200 µm end mill, Harvey Tool, Rowley, Mass.) was connected to a measurement circuit via a ball bearing (McMaster Carr Part #60355K501) attached with conductive epoxy (MG Chemicals 8331) and filled with conductive carbon grease (MG Chemicals 846). A second lead was connected to the animal by placing a wire beneath the skin, or clipping it to a steel head plate. A data acquisition (DAQ) board (National Instruments USB-6001) sent the 100 Hz test signal through the drill bit while simultaneously measuring voltage on the test lead with a 10 kHz sampling rate. The NeuroStar and the data acquisition board were both controlled by a custom Python GUI, written using the PyQt4, PyDAQmx, and PyUSB libraries.

A bearing was attached to the bit as previously described. This was done for two reasons: so that the largest potential drop across the mouse could be detected, and because it was observed that the drill body impedance changed over time. The impedance of the drill was measured as approximately 50 KΩ when new, and 0.6-1.7 MΩ after some wear. This is likely due to wear of the bearings that leads to an increase in contact resistance to the housing (i.e., race) of the bearings.

In order to implement closed-loop craniotomies by modifying a commercial system, it was necessary to replace the drill (optional, but recommended), build an impedance-measurement circuit, and install the Python control GUI. The software was implemented on a Windows computer with Python installed.

Figures 22A, 22B:
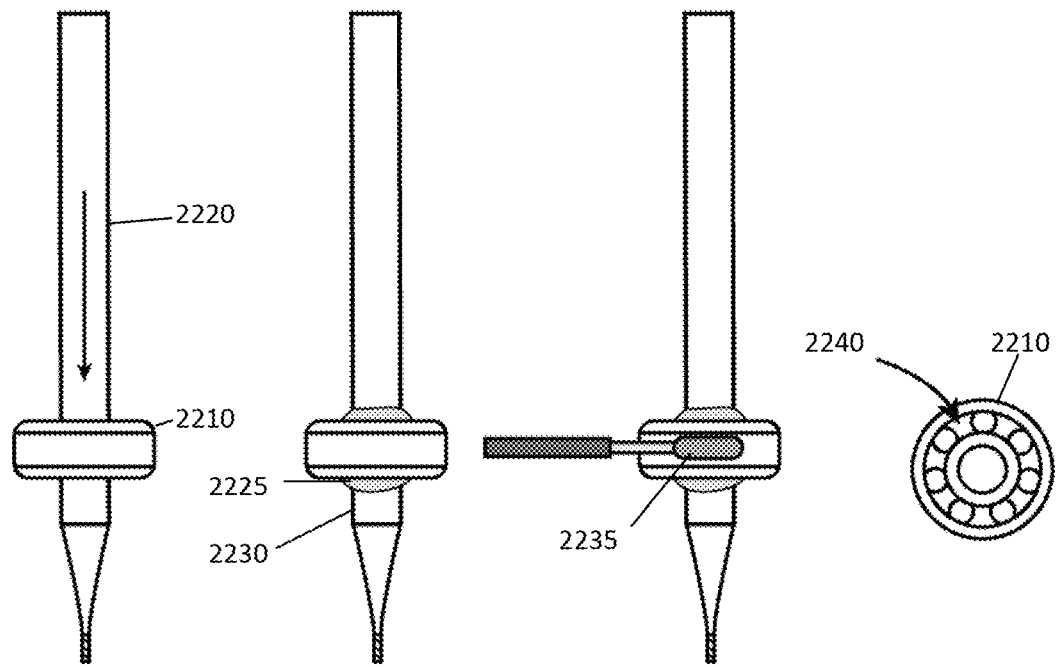
FIGS. 22A-B are side and top views that depict steps for creating an example implementation of the impedance measurement device suitable for use in various implementations of the invention.

FIGS. 22A-B are side and top views of the drill bit, depicting steps for creating an example implementation of the impedance measurement device for use in this version of the invention. First, a wire is connected to the drill bit via a ball bearing. The ball bearing 2210 is slid over the end mill shaft 2220, using conductive epoxy 2225 to connect the inner race of the bearing to the end mil 2230, and a piece of hookup wire 2235 is soldered to the outer face of bearing 2210 (all-purpose flux being necessary to solder stainless steel). The inside 2240 of bearing 2210 is filled with conductive grease, in order to create electrical continuity between end mill 2230 and hookup wire 2235. This modification of the drill bit permits measurements to be taken even when the bit is spinning.

Figure 23:
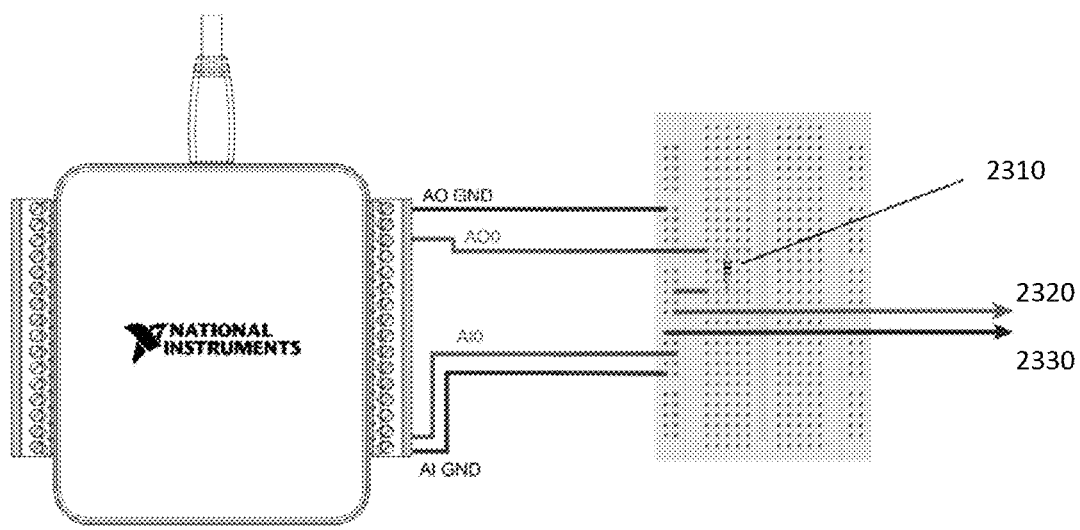

The measurement circuit is constructed using the NI USB-6001 and standard hookup wire. It can either be made with a prototyping breadboard or by soldering wires and a 10 MΩ resistor in the appropriate configuration. FIG. 23 is an example implementation of a measurement circuit useable in this implementation. Shown in FIG. 23 are 10 MΩ resistor 2310, connection wire 2320 to the ball bearing, and connection wire 2330 to the animal.

Table 2 is an example parts list for a specific embodiment of a modified commercial implementation of the present invention.

TABLE 2

| Description | Vendor | Model # |
| --- | --- | --- |
| stereotaxic drill robot | Neuro Star | drill robot |
| electric carving tool | Ram Products | 4161000 |
| 200 µm end mill | Harvey Tool | 13908 |
| ball bearing | McMaster | 60355K501 |
| conductive epoxy | MG Chemicals | 8331 |
| conductive grease | MG Chemicals | 846 |
| DAQ | National Instruments | NI USB 6001 |
| drill holder | custom | |
| 10 MΩ resistor | various | |

An example embodiment of a graphical user interface (GUI) that makes it possible to control the NeuroStar drill from any computer was written in Python and is shown in FIG. 24. The code itself, which represents an example embodiment only, is contained in the computer program listing appendix that has been submitted in computer-readable format as an electronically-filed text file under the provisions of 37 CFR 1.96 and is herein incorporated by reference in its entirety.

Installation. The prototype GUI currently works on Microsoft Windows, due to its dependence on NI-DAQmx for controlling the National Instruments board, but it is clear that implementations on other systems and in other languages are within the skill of the artisan and within the scope of the invention. The standard libraries (e.g. matplotlib, numpy, PyQt4) are utilized. Because the impedance-feedback circuit is so simple, in some embodiments custom hardware may be created for this purpose.

The GUI provides several functionalities through a series of buttons and drop-down menus. These may include, but are not limited to, the following:

Manual control. The left-hand side of the GUI holds buttons for manually moving the 3 axes of the NeuroStar. Each axis has "long" (two arrows) and "short" (one arrow) movement controllers. By default, long steps=1 mm, short steps=20 microns.

"1× distance"—toggles the setting for movement distance; in 0.5× distance mode, long steps=0.5 mm, short steps=10 microns "X"=anterior/posterior control, "Y"=medial/lateral control, "Z"=dorsal/ventral control "Bookmark" button—saves coordinates for returning to later; will prompt the user for a string to label that particular coordinate "Re-center" button—zeros out the axes, so that future coordinates are displayed relative to the current coordinate "Stop" button—prevents the NeuroStar from executing the next movement (it cannot stop the current movement)

The drill may be moved a precise distance along any axis by clicking the "GO TO . . . " button.

Drilling with feedback. The center of the GUI holds the interface for impedance-based feedback. The left plot shows 100 ms of raw data from the test lead connected to the animal. Before the drill has penetrated through the skull, this should show a 100 Hz sine wave, perhaps with some line noise contamination. After penetration, the amplitude of this signal should decrease dramatically, signifying a change in impedance at the drill tip. The right plot shows the frequency-domain representation of the signal. When the power at 100 Hz dips below a threshold (indicated by the bottom of the yellow box overlay), the drill will retract to its original location.

"Drill!"—starts the process of lowering the drill while checking for a 100 Hz threshold crossing. When the threshold is reached, the drill will return to where it was when the button was pressed. Pressing the button a second time will interrupt the process.

"Interval (ms)"—determines how long the software will pause between checking for threshold crossings. The NeuroStar will only move down in Z after every other check (so the movement interval=2× the indicated interval).

"Step size (um)"—determines how far the NeuroStar will move during each movement step. 5 um is the recommended distance when actually drilling through the skull (to prevent unnecessary damage to the underlying brain tissue), but larger increments can be used to position the drill just above the skull surface.

"Amplitude"—determines the amplitude of the sine wave (in volts)

"Threshold"—power at 100 Hz below which indicates the drill has broken through the skull.

The drilling parameters (interval, step size, amplitude, and threshold) can all be adjusted online.

Pattern interface. The left of the GUI holds buttons for programming more complex drill patterns, such as grids and circles.

"Start!"—initiates the process of drilling holes in the pattern currently indicated by the interface "Pattern"—toggles between "circle" and "grid"

"Width (um)"—determines the width of the entire pattern in microns

"Number of points"—the total number of points in the pattern (when in 'grid' mode, there are options for both rows and columns)

As the pattern is being drilled, the software records the Z height of the brain at each point, allowing the user to then interpolate smoothly between all of the points along the path. Interpolation only works well in "circle" mode, and is not meant to be used in "grid" mode.

"Interpolate"—initiates the process of drilling a smooth path between the holes, using the parameters currently indicated by the interface "Interp height"—the height of the interpolated path in microns relative to the measured brain surface (negative=above the surface, positive=below the surface, consistent with the conventions of the Z axis moving up for negative values). The recommended value for avoiding damage while making the skull easy to remove is −20.

"Interp points"—number of points in the interpolation path. Larger numbers=smoother but slower.

"Start" and "end"—by default the interpolation goes around the entire circle (from point 1 back to point 1), but segments may also be manually selected to be drilled at a different depth. This can also be used to re-drill specific holes in the pattern (and thereby re-calculate the Z height at that point).

"Drilling" versus "milling"—toggles between two interpolation patterns, one in which the drill moves vertically through the skull (drilling) and one in which it moves horizontally (milling). Drilling vertically through the bone is highly recommended, as it tends to produce cleaner craniotomies.

Experimental Results (FIGS. 25A-B-28A-B

As previously discussed, the invention leverages the principle that a drill bit passing through the mouse skull encounters a stereotyped increase in conductance with respect to the mouse body. A method based on this information is utilized within the invention to detect skull breakthrough. Both the custom and modified commercially available robotic devices, described earlier, that utilize this method performed automated craniotomies with high precision, high yield, and good safety, with the ability to stop with ~5 micron resolution.

Brain bleeding was not observed in any of the trials performed by the robot once the appropriate conductance threshold was determined. Even minor bleeding can compromise vasculature important for cortical maintenance [Shih A. Y., Blinder P., Tsai P. S., Friedman B, Stanley G, Lyden P D, Kleinfeld D. The smallest stroke: occlusion of one penetrating vessel leads to infarction and a cognitive deficit. Nat Neurosci. 16(1): 55-63, 2013], and release of blood can be neuromodulatory or even toxic to neurons [Yip S., Ip J. K., Sastry B. R. Electrophysiological actions of hemoglobin on rat hippocampal CA1 pyramidal neurons. Brain Res. 713(1-2): 134-142, 1996; Regan R. F., Guo Y. Toxic effect of hemoglobin on spinal cord neurons in culture. J Neurotrauma. 15(8): 645-653, 1998]. Precise control of drill depth obviates such concerns.

FIGS. 25A and 25B depict an example one of the large windows that were created after drilling a series of test holes to account for the curvature of the skull. In this example, holes were drilled at seven points along the circumference of a 3 mm circle, forming the desired window. Impedance-based feedback was used to measure the location of the brain along the z-axis at each point. Then, cubic spline-based interpolation was used to compute the optimal path for the drill to mill a circular pattern in the bone without contacting the underlying tissue.

When the drill broke through the skull (as indicated by a change in conductance), the depth was recorded to obtain a Z depth for each X-Y hole location. Once all of the test holes were drilled, the software computed a trajectory based on cubic spline interpolation of the X, Y, and Z coordinates of each hole (500 points per axis). The drill then followed this trajectory in "open-loop" mode to cut a circular hole in the skull while avoiding damage to the underlying tissue by milling a distance of 20 microns above the measured Z depths.

FIG. 26A-D depict the steps involved in creating two cranial windows in an actual mouse skull. In FIG. 26A, the skull is exposed and cleaned. In FIG. 26B, the center point and diameter of the desired cranial window is manually chosen by the surgeon, and seven holes are automatically drilled along its circumference. In FIG. 26C, the drill automatically interpolates between the hole locations at the appropriate depth, and the skull is manually removed under saline. In FIG. 26D, the steps of FIG. 26A-C are repeated for the opposite hemisphere The system was used to create larger cranial windows up to 5 mm in diameter (N=5 3 mm windows in 4 mice, N=2 5 mm windows in 2 mice). Using a 200 μm square end mill, a series of test holes were drilled around the circumference of the desired window (FIG. 26B). Based on the measured X, Y, and Z coordinates of each hole, the drill was swept along a path that accounted for the curvature of the skull. The bone fragment was then removed under saline, exposing the brain underneath (FIG. 26C). The procedure was repeated for the opposite hemisphere without complications (FIG. 26D). The entire process took approximately 15 minutes for each window (10 minutes to drill the test holes at 1 minute and 20 seconds per hole, and 5 minutes to open the window).

All procedures were in accordance with the National Institutes of Health Guide for the care and use of Laboratory Animals and approved by the Massachusetts Institute of Technology and the Allen Institute for Brain Science Animal Care and Use Committees. Two- to five-month-old C57BL/6 wild-type mice (male) were given general anesthesia using a rodent anesthesia machine with 2% isoflurane in pure oxygen. Animals were placed on a heating pad with a temperature probe to maintain body temperature. After fully non-responsive to foot withdrawal reflex test, mice were administered the analgesics buprenorphine (0.1 mg/kg) and Meloxicam (1-2 mg/kg) subcutaneously. Mice were immobilized in a stereotaxic apparatus with ear bars, and a nose holder and bite bar. Using a scalpel, an incision was made on the scalp to expose the skull, retracting the skin using clips. A small curette was used to retract or remove residual fascia or connective tissue over the area of interest of the skull. Experiments lasted up to 2 hours, with saline only added to soft tissues so that the skull would present a constant dry impedance. Experiments were terminal. After the end of each experiment performed with the custom-built system, skulls were removed, and craniotomy diameters were measured using an x-ray micro-computed tomography system (XT H 160, Nikon, Tokyo, Japan).

When the drill tip came in contact with the skull surface, the observed electrical current was negligible, due to the small conductance of the skull (<0.10 nS; measured with an LCR meter, 4263B, Agilent, Santa Clara, Calif.). However, when the drill tip penetrated the skull, the conductance between the drill bit and the body dramatically increased due to the high conductivity of cerebrospinal fluid. To quantify this effect as a function of frequency, the electrical impedance was measured between a dental drill and the body of a mouse as the drill created a craniotomy, using a custom circuit (FIG. 2) that performed this measurement. A simple robot was constructed to lower the drill bit (FIG. 5) in a controlled fashion (FIGS. 3, 4). A sinusoidal test signal was delivered to the drill, and measured the voltage amplitude and phase angle across the mouse as a 500 μm diameter dental burr was passed through the skull, for eight different signal frequencies from 30-100,000 Hz (2, 5, 6, 10, 15, 18, and 19 sweeps per mouse). It was found that the voltage was sensitive to drill depth through the skull over a broad range of frequencies from 30 Hz to 1 kHz (n=7 mice; FIG. 6A, voltage data; FIG. 6B, calculated conductance data). Based on these data, a frequency of 100 Hz was chosen because it showed the largest electric potential drop as the drill bit passed through the skull.

Using a 100 Hz sinusoidal voltage, the time course of the conductance changes as the drill advanced through the skull was examined. FIG. 27A is a graph of normalized electric potential vs. distance traveled, for 10 holes in one mouse skull, each represented by a different color (step size 5 μm, frequency 100 Hz). Traces were aligned (at distance=0) at the point in the curve of maximum slope. FIG. 27B is a graph of electrical conductance vs. distance traveled (as in FIG. 27A) for all 10 craniotomies (n=10 holes in one mouse skull).

Using the robot of FIGS. 2-4, it was observed that (for each craniotomy) conductance is near zero for most of the drilling process, then jumps significantly to a higher conductance over a small number of steps, and then remains high for subsequent steps of the drill. This indicates that conductance does not vary appreciably as the skull is thinned, but instead rises suddenly when the drill passes slightly through the inner surface of the skull. It was necessary to determine whether a precise threshold for the conductance could be derived, so that the robot would stop when it completed the craniotomy without damaging the brain.

Figure 28A:
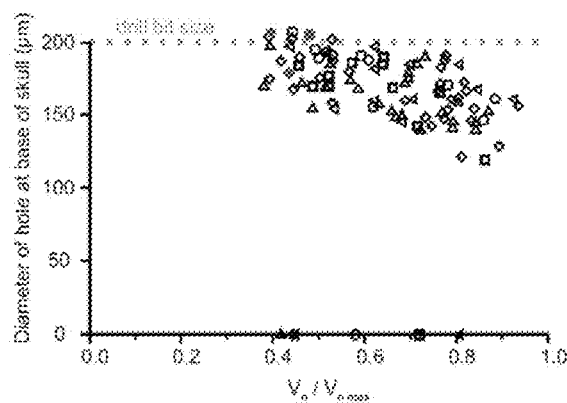
Figure 28B:
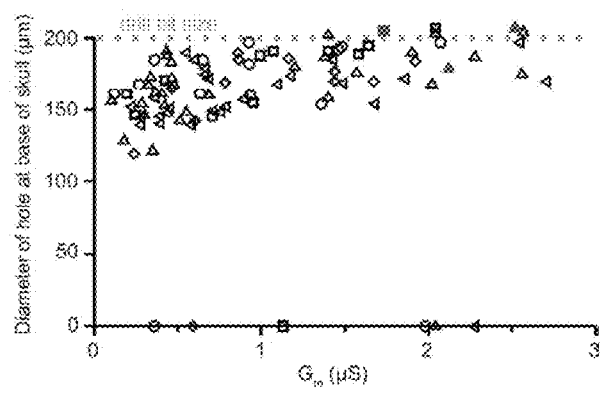

FIG. 28A is a plot of hole size, measured at the base of the skull, measured using x-ray micro-computed tomography (CT), as a function of final normalized electric potential, with the drill stopping when various normalized electrical potentials were reached. n=98 craniotomies in 5 mice; 200 μm drill bit (width indicated by dotted line). Each mouse is represented by a different shape, with red fill indicating visible blood arising near the stopping point. For 6 of the 98 craniotomies, the drill bit did not pass the bottom of the skull, and thus are on the y=0 line. FIG. 28B is a plot of hole size vs. electrical conductance, for the data of FIG. 28A.

The robot was operated with a 200 μm drill bit, stopping the drilling when various drill-to-mouse electrical potentials (FIG. 28A, normalized; FIG. 28B, calculated conductances) were achieved. For each trial, the craniotomy diameter at the base of the skull was measured. As the normalized electrical potential threshold was lowered systematically (from ~0.95 down to ~0.3), the hole diameters increased, from under 150 mm to around 200 mm (n=98 craniotomies in 5 mice). The electric potential and hole diameter were inversely correlated (FIG. 28A, correlation coefficient r=−0.61, p=1.26× $10^{-7}$) with lower potential being associated with larger hole diameters. In 6 of the 98 cases, the experiment was stopped because of hitting a blood vessel in the skull—a benign, but unavoidable, occasional event that yielded zero-diameter holes. In a small minority of cases, the drill successfully created a craniotomy but produced bleeding, suggesting a sub-optimal craniotomy, perhaps related to damage caused by the use of a standard pointed drill bit (red symbols, FIGS. 28A-B). A threshold for the drill was chosen that was high enough so that bleeding could be avoided, but small enough to maximize hole size. For the particular 200 μm diameter drill bits that were used in these experiments, it was found that a normalized electric potential threshold value of 0.65 yielded a good balance.

In the experiments of FIGS. 27A-B and 28A-B, the circuit works by sending a sine wave from a function generator (20 V, 100 Hz) through a sense resistor (681 kW) and a wire in contact with the drill body. The cable conducts the electrical signal from the function generator to the drill and from the mouse back to the DAQ. This cable consisted of a pair of twisted wires. The rear paw of the mouse made electrical contact to the ground lead of this cable connected to the ground pin of the DAQ through a piece of metal touching the skin of the paw, and held stationary by a test clip whose spring had been stretched to make it weaker.

The DAQ measures $V_n$ as follows: the Lab VIEW program records the maximum and minimum value of ten sinusoidal waves, each consisting of 1,500 samples at 25 kHz. It subtracts the minimum value from the maximum and averages these ten to estimate the peak-to-peak amplitude of the voltage drop across the mouse. These two methods only work when the signal amplitude is much higher than the noise, which is the case when there is a large driving current. The impedance of the drill was included in the circuit because the simplest method for sending a signal through the drill is to connect a wire to the body of the drill, which is conductive to the drill bit. This impedance would show up as a resistor in series with the mouse in FIG. 2. Electric potential measurements were made in discrete steps. The solenoid valve was turned on for 300 µs, a step of 5 µm was taken, a pause of 3.5 s allowed the drill to come to a complete stop, and then a measurement was taken for 0.6 s.

The use of robotic craniotomy robots with this skull breakthrough detection method allows many small precisely-spaced craniotomies to be drilled, which may be useful for deploying multi-injector [Chan, S. Y., Bernstein, J. G., Boyden, E. S. Scalable Fluidic Injector Arrays for Viral Targeting of Intact 3-D Brain Circuits. J Vis Exp. 35: 1489, 2010], multi-electrode [Recce, M., and J. O'Keefe. The tetrode: a new technique for multi-unit extracellular recording. Soc Neurosci Abstr. 15(2), 1989; Maynard, Edwin M., Craig T. Nordhausen, and Richard A. Normann. The Utah intracortical electrode array: a recording structure for potential brain-computer interfaces. Electroencephalogr Clin Neurophysiol 102 (3): 228-239, 1997], or multi-optical fiber probes [Zorzos, A. N., Scholvin, J., Boyden, E. S., & Fonstad, C. G. Three-dimensional multiwaveguide probe array for light delivery to distributed brain circuits. Opt Lett. 37(23): 4841-4843, 2012] for interrogating distributed neural circuits. The smallest size of craniotomy possible with the technique presented here is limited by the size of available bits, which currently go down to 50 µm, but it may be possible to create custom tools that are even smaller. It is extremely difficult for human surgeons to handle drill bits of this size, making a robotic device a practical solution when holes of this size are desired.

Previous techniques are either more expensive or less precise than this method. Furthermore, this technique can be easily adapted to an existing surgery setup that a lab already has. This method for automated opening of craniotomies will be accessible to a wide range of neuroscientists. The method works equally well on custom-built systems and modified commercially available drilling systems. Because the technique is conceptually simple, it should be straightforward to adapt it to alternate setups.

Automated craniotomies should not be thought of as a replacement for human surgeons, but rather as a useful addition to the surgical toolkit. The method still requires a human to place the mouse in a stereotaxic device, expose the skull, and align the drill with the appropriate structures. Using the technique for automated craniotomies should result in more consistent holes with smaller diameters and tighter spacing than previously possible. Furthermore, the opening of large cranial windows—something that typically requires extensive training—can now be performed automatically. And if multiple surgical robots are set up in the same laboratory, the same number of experimenters can perform more surgeries in less time. As the tools for neural recording and stimulation become increasingly sophisticated, it is important to eliminate variability in craniotomy quality as a potential failure mode for these devices. The use of conductance-based feedback is an effective way to improve the reliability of the holes needed to expose the brain prior to inserting pipettes, electrodes, and fiber optic cables, or for the purpose of imaging neural tissue.

While preferred embodiments of the invention are disclosed herein, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention.

What is claimed is:

1. An automated craniotomy opening apparatus, comprising:
   a craniotomy drilling apparatus having a drilling tip;
   at least one craniotomy drilling apparatus positioning device connected to the craniotomy drilling apparatus;
   a detection device connected to the drilling tip; and
   a computer processor specially configured and connected to automatically and iteratively control the craniotomy drilling apparatus, the craniotomy drilling apparatus positioning device, and the detection device, the computer processor programmed to automatically open a craniotomy, without user intervention, by:
      positioning the drilling tip with respect to the target skull at a predetermined position for drilling;
      drilling into the target skull with the drilling tip for a predetermined distance;
      after drilling, automatically determining the conductance near the drilling tip using the detection device;
      if the conductance is below a predetermined threshold, automatically returning the drilling tip to a home position; and
      if the conductance is not below the predetermined threshold, automatically repeating drilling for the predetermined distance and determining the conductance until the conductance exceeds the predetermined threshold.

2. The apparatus of claim 1, wherein the detection device includes an impedance detection circuit.

3. The apparatus of claim 2, wherein the impedance detection circuit comprises:
   a signal source;
   a sense resistor in series with the signal source; and
   an output for sending the detected impedance to the computer processor.

4. The apparatus of claim 2, wherein determining the conductance comprises:
   under the control of the computer processor,
      measuring impedance with the impedance detection circuit; and
      calculating the conductance using the measured impedance.

5. The apparatus of claim 4, wherein measuring impedance comprises:
   under the control of the computer processor,
      sending a signal through the impedance detection circuit to the drilling tip;
      detecting a voltage at the target skull; and
      sending a signal representing the detected voltage from the impedance detection circuit to the computer processor.

6. The apparatus of claim 5, wherein calculating the conductance comprises determining a voltage drop across the impedance detection circuit.

7. The apparatus of claim 4, wherein measuring impedance comprises the steps of:
  under the control of a computer processor,
   sending a signal at a predetermined voltage through the impedance detection circuit to the target skull;
   detecting a voltage at the drilling tip; and
   sending a signal representing the detected voltage from the impedance detection circuit to the computer processor.

8. The apparatus of claim 7, wherein calculating comprises determining a voltage drop across the impedance detection circuit.

9. The apparatus of claim 1, wherein the detection device is attached to the drilling tip in a manner that permits measurements to be made while the drilling apparatus is running.

10. The apparatus of claim 1, wherein the drilling tip is a blunt-tipped end mill.

11. The apparatus of claim 1, wherein the craniotomy drilling apparatus positioning apparatus is a motorized stereotaxic stage connected to the drilling apparatus.

12. The apparatus of claim 1, wherein a drill hole pattern comprising a plurality of craniotomies to be drilled in the target skull is predetermined and the drill hole pattern is created by drilling the plurality of craniotomies using the apparatus of claim 1.

13. The apparatus of claim 12, wherein the predetermined drill hole pattern is selected to facilitate creation of a cranial window in the target skull.

14. The apparatus of claim 13, wherein the cranial window is created by drilling along a path that interpolates between the holes to form a circumference of the cranial window.

* * * * *